United States Patent
Downie et al.

(10) Patent No.: US 9,581,297 B2
(45) Date of Patent: Feb. 28, 2017

(54) METHOD OF, AND APPARATUS FOR, MEASURING THE TRUE CONTENTS OF A CYLINDER OF GAS UNDER PRESSURE

(71) Applicant: Air Products and Chemicals, Inc., Allentown, PA (US)

(72) Inventors: Neil Alexander Downie, Hampshire (GB); Clayton Mathew Ludik, Twickenham (GB)

(73) Assignee: Air Products and Chemicals, Inc., Allentown, PA (US)

( * ) Notice: Subject to any disclaimer, the term of this patent is extended or adjusted under 35 U.S.C. 154(b) by 0 days.

(21) Appl. No.: 14/402,504

(22) PCT Filed: May 23, 2013

(86) PCT No.: PCT/EP2013/060689
§ 371 (c)(1),
(2) Date: Nov. 20, 2014

(87) PCT Pub. No.: WO2013/174957
PCT Pub. Date: Nov. 28, 2013

(65) Prior Publication Data
US 2015/0128682 A1    May 14, 2015

(30) Foreign Application Priority Data
May 24, 2012  (EP) .................................... 12169387

(51) Int. Cl.
*G01N 29/02* (2006.01)
*G01N 29/036* (2006.01)
(Continued)

(52) U.S. Cl.
CPC ............. *F17C 13/04* (2013.01); *G01N 9/002* (2013.01); *G01N 29/022* (2013.01);
(Continued)

(58) Field of Classification Search
CPC ................ G01F 1/86; G01N 2291/014; G01N 2291/021; G01N 2291/02818;
(Continued)

(56) References Cited

U.S. PATENT DOCUMENTS 3,561,832 A    2/1971    Karrer et al.
3,612,966 A    10/1971   Dybel
(Continued)

FOREIGN PATENT DOCUMENTS

CN    1240024       12/1999
CN    1287616 A     3/2001
(Continued)

OTHER PUBLICATIONS

Zeisel et al., "A Precise and Robust Quartz Sensor Based on Tuning Fork Technology for (SF6)—Gas Density Control", Sensors and Actuators, 2000, pp. 233-236.
(Continued)

*Primary Examiner* — Peter Macchiarolo
*Assistant Examiner* — Jamar Ray
(74) *Attorney, Agent, or Firm* — Larry S. Zelson

(57) ABSTRACT

There is provided a sensor assembly (200) for measuring physical properties of a gas under pressure within a pressure vessel (100). The sensor assembly (200) comprises a housing and a piezoelectric oscillator (202) for immersion in the gas within the pressure vessel (100). The sensor assembly (200) is arranged, when immersed in said gas, to measure the density of the gas within the pressure vessel (100). The housing comprises a first chamber and a second chamber. The first chamber is in fluid communication with the second chamber and substantially encloses said piezoelectric oscillator. The second chamber is in fluid communication with the interior of the pressure vessel. By providing such an arrangement, the true contents (i.e. mass) of fluid in a (Continued)

pressure vessel such as a cylinder can be measured directly and accurately. The housing of the present invention alleviates noise and errors generated by convective currents within a gas cylinder 100, enabling an accurate determination of mass, or rate of change of mass. through direct derivation from the density of the gas in the cylinder.

13 Claims, 16 Drawing Sheets

(51) Int. Cl.
*G01N 9/00* (2006.01)
*F17C 13/04* (2006.01)
*G01F 1/86* (2006.01)

(52) U.S. Cl.
CPC ............. *G01N 29/036* (2013.01); *G01F 1/86* (2013.01); *G01N 2291/014* (2013.01); *G01N 2291/021* (2013.01); *G01N 2291/02818* (2013.01); *G01N 2291/0426* (2013.01); *G01N 2291/0427* (2013.01)

(58) Field of Classification Search
CPC ... G01N 2291/0426; G01N 2291/0427; G01N 29/022; G01N 29/036; G01N 9/002; G01N 11/16; G01N 2009/006; G01N 29/2437; G01N 29/2443; G01N 29/245; F17C 13/04; H01H 33/563
See application file for complete search history.

(56) References Cited

U.S. PATENT DOCUMENTS

| | | | |
|---|---|---|---|
| 3,902,355 | A | 9/1975 | Weisser |
| 4,126,049 | A | 11/1978 | Cotter |
| 4,232,544 | A | 11/1980 | Stansfeld |
| 4,275,393 | A | 6/1981 | Johnston |
| 4,507,970 | A | 4/1985 | Dinger |
| 4,526,480 | A | 7/1985 | Ward |
| 4,644,796 | A | 2/1987 | Ward |
| 4,644,804 | A | 2/1987 | Ramm et al. |
| 4,680,970 | A | 7/1987 | Ueda et al. |
| 4,713,774 | A | 12/1987 | Funk et al. |
| 4,724,707 | A | 2/1988 | Innerhofer |
| 4,734,609 | A | 3/1988 | Jasmine |
| 4,741,213 | A | 5/1988 | Hojoh |
| 4,747,311 | A | 5/1988 | Hojoh |
| 4,938,068 | A | 7/1990 | Clements |
| 4,995,263 | A | 2/1991 | Stocker |
| 5,136,885 | A | 8/1992 | Liebermann et al. |
| 5,220,836 | A | 6/1993 | Harms et al. |
| 5,235,844 | A | 8/1993 | Bonne et al. |
| 5,307,668 | A | 5/1994 | Vander Heyden |
| 5,307,683 | A | 5/1994 | Phelps et al. |
| 5,421,190 | A | 6/1995 | Brandle et al. |
| 5,471,882 | A | 12/1995 | Wiggins |
| 5,659,129 | A * | 8/1997 | Asoyan et al. ............... 73/54.25 |
| 5,900,534 | A * | 5/1999 | Miller et al. ................. 73/24.05 |
| 5,954,089 | A | 9/1999 | Seymour |
| 6,003,543 | A | 12/1999 | Sulatisky et al. |
| 6,230,731 | B1 | 5/2001 | Miller et al. |
| 6,266,996 | B1 | 7/2001 | Livingston |
| 6,286,361 | B1 | 9/2001 | Jones et al. |
| 6,532,822 | B1 | 3/2003 | Boyd |
| 7,444,878 | B1 | 11/2008 | Pepples |
| 7,454,952 | B2 | 11/2008 | Kita et al. |
| 2003/0053516 | A1 | 3/2003 | Atherton |
| 2007/0068493 | A1 | 3/2007 | Pavlovsky |
| 2007/0186982 | A1 | 8/2007 | Cohen et al. |
| 2008/0184804 | A1 | 8/2008 | Leverrier et al. |
| 2009/0151461 | A1 | 6/2009 | Ishii |
| 2010/0107735 | A1 | 5/2010 | Pavlovsky |
| 2010/0132471 | A1 | 6/2010 | Hedtke et al. |
| 2010/0269365 | A1 | 10/2010 | Miller et al. |
| 2011/0126930 | A1 | 6/2011 | Hayashi et al. |
| 2012/0000559 | A1 | 1/2012 | Mussot |
| 2012/0256086 | A1 | 10/2012 | Husebo et al. |
| 2013/0042698 | A1 | 2/2013 | Mayr et al. |

FOREIGN PATENT DOCUMENTS

| | | |
|---|---|---|
| CN | 1768312 A | 5/2006 |
| CN | 101708437 A | 5/2010 |
| CN | 101761779 A | 6/2010 |
| CN | 101881640 A | 11/2010 |
| CN | 202061563 U | 12/2011 |
| CN | 102472653 A | 5/2012 |
| CN | 202212112 U | 5/2012 |
| DE | 3345750 A1 | 6/1985 |
| DE | 3641842 A1 | 6/1988 |
| DE | 10232823 A1 | 11/2003 |
| DE | 102010028475 A1 | 11/2011 |
| EP | 0101669 A2 | 2/1984 |
| EP | 0129753 A1 | 2/1985 |
| EP | 0273649 A2 | 7/1988 |
| EP | 0484569 A1 | 5/1992 |
| EP | 0582045 B1 | 5/1993 |
| EP | 0671680 A1 | 9/1995 |
| EP | 1930709 A1 | 11/2008 |
| GB | 1349256 A | 4/1974 |
| JP | 58151517 | 8/1983 |
| JP | 1170824 A | 7/1989 |
| JP | 3068828 A | 3/1991 |
| JP | 09155180 A | 6/1997 |
| JP | 10010031 | 1/1998 |
| JP | 2002122498 A2 | 4/2002 |
| JP | 2004286514 A | 10/2004 |
| JP | 2005506495 | 3/2005 |
| JP | 2005241355 | 9/2005 |
| JP | 2007244946 A | 9/2007 |
| JP | 2009198472 A2 | 9/2009 |
| JP | 2010038867 A | 2/2010 |
| JP | 2015520853 A | 7/2015 |
| JP | 2015526653 A | 9/2015 |
| JP | 2015526694 A | 9/2015 |
| JP | 2015526695 A | 9/2015 |
| JP | 2015526773 A | 9/2015 |
| TW | M334632 Y | 6/2008 |
| TW | 201118290 | 6/2011 |
| TW | 201207339 | 2/2012 |
| WO | 9802686 A1 | 1/1998 |
| WO | 9940553 A1 | 8/1999 |
| WO | 2007002288 A2 | 1/2007 |
| WO | 2007050400 A1 | 5/2007 |
| WO | 2011039534 A1 | 4/2011 |
| WO | 2011138147 A1 | 10/2011 |

OTHER PUBLICATIONS

The European Patent Office, Written Opinion of the International Searching Authority, mailed Dec. 4, 2014, for PCT/EP2013/060689.
Zeisel, D., H. Menzi and L. Ullrich "A precise and robust quartz sensor based on tuning fork technology for (SF6)-gas density control", Sensors and Actuators 80, pp. 233-236 (2000).
TRAFAG AG data sheets "8773 Density Sensor"(4 pp.) from 1999 (brochure date Apr. 1999).
Decision of the German Federal Patents Court in the matter 20 W (pat) 357/04, handed down on Oct. 12, 2009 and retrievable shortly thereafter on the internet on the home page of the German Federal Patents Court.
Density Sensor 8774 data sheet from Trafag AG, date Jan. 2006.
European Patent Office, International Search Report of the International Searching Authority, mailed Jul. 18, 2013, for PCT/EP2013/060686.
European Patent Office, International Search Report of the International Searching Authority, mailed Aug. 2, 2013, for PCT/EP2013/060689.
Suzuki, et al., "GD Vibratory Gas Density Meters", Yokogawa Technical Report, 2000, No. 20.

(56) References Cited

OTHER PUBLICATIONS

Suzuki, Jun-ichi, "GD Series Vibratory Gas Density Meters", Yokogawa Technical Report English Edition, No. 29 (2000), pp. 23-26.

Sell, Johannes K., "Real-time monitoring of a high pressure reactor using a gas density sensor", Sensors and Actuators A: 162 (2010) 215-219.

Annex A: Documents cited in Opposition proceedings, included in letter from Beck Greener, Jun. 10, 2015 (References cited on IDS filed Nov. 13, 2015).

* cited by examiner

METHOD OF, AND APPARATUS FOR, MEASURING THE TRUE CONTENTS OF A CYLINDER OF GAS UNDER PRESSURE

The present invention relates a method of, and apparatus for, measuring the true contents of a cylinder of gas under pressure. More particularly, the present invention relates to a method of, and apparatus for, accurately measuring the true contents, or rate of change of true contents, of a cylinder of gas using a piezoelectric oscillator and shielding housing.

The methods and apparatus described herein can be applied to systems where gas of relatively high pressure (e.g. about 10 bar or higher) are present, such as for example, the supply of gases in high pressure cylinders or manufacturing plants utilising high pressure gases. The present invention relates particularly to "clean" gases, i.e. gases with little or no impurities or contaminants such as water vapour or dust.

A compressed gas cylinder is a pressure vessel designed to contain gases at high pressures, i.e. at pressures significantly greater than atmospheric pressure. Compressed gas cylinders are used in a wide range of markets, from the low cost general industrial market, through the medical market, to higher cost applications, such as electronics manufacture utilising high purity corrosive, toxic or pyrophoric speciality gases. Commonly, pressurised gas containers comprise steel, aluminium or composites and are capable of storing compressed, liquefied or dissolved gases with a maximum filling pressure up to 450 bar g (where bar g is a measure of the pressure (in bar) above atmospheric pressure) for most gases, and up to 900 bar g for gases such as hydrogen and helium.

The present invention is particularly applicable to permanent gases. Permanent gases are gases which cannot be liquefied by pressure alone, and for example can be supplied in cylinders at pressures up to 450 bar g. Examples are Argon and Nitrogen. However, this is not to be taken as limiting and the term gas may be considered to encompass a wider range of gases, for example, both a permanent gas and a vapour of a liquefied gas. Vapours of liquefied gases are present above the liquid in a compressed gas cylinder. Gases which liquefy under pressure as they are compressed for filling into a cylinder are not permanent gases and are more accurately described as liquefied gases under pressure or as vapours of liquefied gases. As an example, nitrous oxide is supplied in a cylinder in liquid form, with an equilibrium vapour pressure of 44.4 bar g at 15° C. Such vapours are not permanent or true gases as they are liquefiable by pressure or temperature around ambient conditions.

In many instances, it is necessary to monitor the contents of a given cylinder or pressure vessel to determine the amount of gas remaining. This is particularly critical in situations such as health care applications.

It is known to calculate, in accordance with the gas laws, the true contents of a cylinder from knowledge of the pressure of gas within a cylinder. Pressure measurement is a well known art and there are a variety of devices which function to measure pressure. The most conventional type uses an elastic diaphragm equipped with strain gauge elements. However, although one of the lowest cost pressure sensors currently made, these sensors tend to be relatively large in size, and have a mechanical structure which although producible by mass-production photolithographic methods is still relatively complex and expensive to make. They also have a certain degree of fragility and require calibration and temperature compensation before they can be used.

Another commonly used pressure gauge is a Bourdon gauge. Such a gauge comprises a fragile, flattened thin-wall, closed-ended tube which is connected at the hollow end to a fixed pipe containing the fluid pressure to be measured. An increase in pressure causes the closed end of the pipe to describe an arc. Such a gauge comprises delicate components which are vulnerable to damage from, for example, exposure to high pressures.

One problem that makes it difficult to accurately measure the amount of gas in a gas vessel is the temperature-pressure relationship of gases contained within the cylinder. According to the gas laws, the pressure exerted by a given quantity of gas at constant volume is directly proportional to its temperature. Therefore, as the temperature of a gas increases, so will the pressure of the gas.

Consequently, the measurement of pressure using a pressure gauge such as a Bourdon gauge goes up and down proportionally to absolute temperature, e.g. from an initial temperature of 20° C. to, for example, 50° C. in an sunlit environment, the indicated pressure on a Bourdon gauge will increase by 10%.

An additional issue is that, in order to determine the contents of a cylinder using a pressure measurement, the pressure gauge is required to be corrected for compressibility of the gas. This is complicated by the behaviour of a gas at high pressure not conforming to the behaviour of an ideal gas.

An alternative type of device used to measure the physical properties of gases is a piezoelectric device such as a quartz crystal. Quartz crystals demonstrate piezoelectric behaviour, i.e. the application of voltage to them results in slight squeezing or stretching of the solid, and vice versa.

"*A Precise And Robust Quartz Sensor Based On Tuning Fork Technology For ($SF_6$)—Gas Density Control*" Zeisel et al, Sensors and Actuators 80 (2000) 233-236 discloses an arrangement whereby a quartz crystal sensor is used to measure the density of $SF_6$ gas in high and medium voltage electrical equipment at low gas pressures. The measurement of the density of the $SF_6$ gas is critical to the safety of the apparatus. This document describes a low pressure application for quartz sensor technology in which pressures of up to 8 bar g are used.

U.S. Pat. No. 4,644,796 discloses a method and apparatus for measuring the pressure of a fluid using a quartz crystal oscillator housed within a variable-volume housing comprising a bellows arrangement. The internal volume of the housing varies due to compression/expansion of the bellows by external fluid pressure. Consequently, the density of the fluid within the housing varies as the internal volume of the housing varies. The density within the housing can be measured using a quartz crystal oscillator.

The above arrangements describe the use of a solid state sensor such as a quartz crystal oscillator. However, neither of the above arrangements and methods is suitable for accurately measuring the mass of gas in a pressure vessel such as a gas cylinder.

An additional complication with regard to the measurement of the physical properties of a gas contained in a gas cylinder is the motion of the gas within the cylinder. For example, if the top of a gas cylinder is cold, vigorous convections currents can be set up which can distort the measurements of the physical properties of the gas.

The Grashof number (Gr) is a dimensionless number which approximates the ratio of the buoyancy to the viscous force acting on a fluid. The value of Gr provides an indication the likelihood of the occurrence of convection in particular fluids—the higher the value of Gr, the more likely convection is to occur.

The value of Gr of, for example, Argon gas at a pressure of 300 bar g pressure within a gas cylinder is very large. Argon at such high pressures has a density approaching that of water but has a significantly lower viscosity (approximately fifty times lower than water). In addition, Argon has a much greater tendency to expand when heated than water. As a result, even small negative temperature gradients (i.e. where the top of the cylinder is colder) can lead to strong convection of the gas within the gas cylinder.

A temperature gradient along the length of a cylinder may occur in a number of circumstances in use. For example, if a cylinder has been recently filled, if it is moved between environments at different temperatures, or in a situation where a flow is drawn from a valve attached to the cylinder, the top of the cylinder may be significantly colder than the bulk of the cylinder. The temperature gradient may be often more than 10° C. and even as high as 30° C. At present, integrated pressure reduction valves (VIPRs) are becoming increasingly popular.

However, such valves get particularly cold as they expand the gas from the storage pressure. Therefore, as a result of these temperature differences, convection will often take place in a cylinder. The convection takes place in a turbulent way, with random modulations of density and temperature, such that $\rho \sim 1/T$, with almost no change in pressure.

In general, one approach to measure the physical properties of a gas within a cylinder is to place a sensor inside the gas cylinder itself. This enables the sensor to monitor gas properties at the centre of the cylinder.

However, when flow is drawn from a gas cylinder using a cylinder having a VIPR, strong convection currents are generated. Convection currents lead to excessive noise when measuring gas properties such as the rate of change of mass contents of a cylinder, rendering measurement results inaccurate or even meaningless. Therefore, known measuring arrangements suffer from a technical problem that they are unable to provide accurate measurement of the physical properties of a gas in an enclosure such as a gas cylinder where convection is likely to be encountered.

According to a first aspect of the present invention, there is provided a sensor assembly for measuring physical properties of a gas under pressure within a gas cylinder comprising a gas cylinder body and a valve arrangement defining a fixed internal volume of the gas cylinder, the sensor assembly comprising a housing, a piezoelectric oscillator for immersion in the gas within the gas cylinder and a drive circuit operable to drive the piezoelectric oscillator such that the piezoelectric oscillator resonates at a resonant frequency, the sensor assembly being arranged to determine the density of the gas within the gas cylinder from the resonant frequency of the piezoelectric oscillator when immersed in said gas, wherein, in use, the housing is located within the fixed internal volume of the gas cylinder and comprises a first chamber and a second chamber, the first chamber being in fluid communication with the second chamber and substantially enclosing said piezoelectric oscillator, and the second chamber being in fluid communication with the interior of the gas cylinder.

The arrangement of the present invention relates to a sensor assembly. The sensor assembly includes a piezoelectric oscillator enclosed within a housing. The housing is a self-contained structure comprising at least two chambers and is arranged to be placed within a pressure vessel such as a gas cylinder. This enables optimal placement of the sensor assembly within the pressure vessel, where it may be, for example, spaced from the walls of the vessel where temperature variations or boundary layer flow may affect, for example, density measurement.

According to an embodiment, there is provided a sensor assembly for measuring physical properties of a gas under pressure within a pressure vessel, the sensor assembly comprising a housing and a piezoelectric oscillator for immersion in the gas within the pressure vessel, the piezoelectric oscillator being arranged, when immersed in said gas, to measure the density of the gas within the pressure vessel, wherein the housing comprises a first chamber and a second chamber, the first chamber being in fluid communication with the second chamber and substantially enclosing said piezoelectric oscillator, and the second chamber being in fluid communication with the interior of the pressure vessel.

By providing such an arrangement, the true contents (i.e. mass) of fluid in a pressure vessel such as a cylinder can be measured directly without the need to compensate for factors such as temperature or compressibility. The housing of the present invention alleviates noise and errors generated by convective currents within a gas cylinder, enabling an accurate determination of mass, or rate of change of mass through direct derivation from the density of the gas in the cylinder.

Further, the piezoelectric oscillator is a solid state device which is resistant to high pressures or sudden changes in pressure and, as such, is less likely to become damaged by pressure "creep" or other environmental factors. The structure of the piezoelectric oscillator enables the piezoelectric oscillator to be entirely immersed in the gas, in contrast to conventional gauges (such as a Bourdon gauge) which requires a pressure differential in order to function.

In one embodiment, the sensor assembly further comprises a drive circuit operable to drive the piezoelectric oscillator such that the piezoelectric oscillator resonates at a resonant frequency and to measure said resonant frequency over a pre-determined time period to determine the density of gas in said pressure vessel.

In one embodiment, the pressure vessel has a fixed internal volume and the sensor assembly is further configured to determine, from the density measurement and from the internal volume of said pressure vessel, the mass of the gas within the pressure vessel.

In one embodiment, the sensor assembly is further arranged to perform repeat measurements of the mass of the gas within the pressure vessel at discrete time intervals to obtain a plurality of measurements, and to determine, from said plurality of measurements, the mass flow of gas to/from the pressure vessel during the discrete time intervals.

In one embodiment, the discrete time intervals are of the order of seconds.

In one embodiment, numerical filtering is applied to said measurements.

In one embodiment, the first chamber has a wall comprising a first aperture enabling fluid communication between the first and second chambers, and the second chamber has a wall comprising a second aperture to enable fluid communication between the second chamber and the interior volume of the pressure vessel.

In one embodiment, the first and/or second aperture has dimensions of 0.35 mm or less.

In one embodiment, the first and/or second aperture has dimensions of 0.22 mm or less.

In one embodiment, the housing is substantially cylindrical.

In one embodiment, the housing has a length of 230 mm or less.

In one embodiment, the housing has a length of 80 mm or less.

In one embodiment, said piezoelectric oscillator comprises a quartz crystal oscillator.

According to a second aspect of the present invention, there is provided a gas cylinder for containing a gas under pressure, the gas cylinder comprising: a gas cylinder body defining a fixed internal volume; a valve arrangement connected to said gas cylinder body and arranged to enable selective filling of the gas cylinder with gas or dispensation of gas from said gas cylinder ; and the sensor assembly of the first aspect.

According to an embodiment, there is provided a pressure vessel for containing a gas under pressure, the pressure vessel having a fixed internal volume and comprising: a pressure vessel body defining a fixed internal volume; a valve arrangement connected to said vessel body and arranged to enable selective filling of the pressure vessel with gas or dispensation of gas from said vessel; and the sensor assembly of the first aspect.

In one embodiment, the sensor assembly is located entirely within the fixed internal volume of the pressure vessel.

In one embodiment, the pressure vessel is in the form of a gas cylinder.

According to a third aspect of the present invention, there is provided a method of measuring the mass of a gas under pressure using a sensor assembly comprising a piezoelectric oscillator and a housing, said gas being contained within a pressure vessel having a fixed internal volume, the piezoelectric oscillator being immersed in the gas within the pressure vessel, the housing comprises a first chamber and a second chamber, the first chamber being in fluid communication with the second chamber and substantially enclosing said piezoelectric oscillator, and the second chamber being in fluid communication with the interior of the pressure vessel, the method comprising: a) utilising said piezoelectric oscillator to measure the density of the gas within the high-pressure vessel; b) determining, from the density measurement and from the internal volume of said pressure vessel, the mass of the gas within the pressure vessel.

By providing such a method, the true contents (i.e. mass) of gas (such as a permanent gas) in a pressure vessel such as a cylinder can be measured directly without the need to compensate for factors such as temperature or compressibility. This allows a determination of mass through direct derivation from the density of the gas in the cylinder, reducing the need for additional sensors or complex compensations and approximations to be made. Further, the piezoelectric oscillator is a solid state device which is resistant to high pressures, sudden changes in pressure or other environmental factors. The piezoelectric oscillator is operable to be entirely immersed in the gas, in contrast to conventional gauges (such as a Bourdon gauge) which requires a pressure differential in order to function.

In one embodiment, step a) comprises: driving, by means of a drive circuit, the piezoelectric oscillator such that the piezoelectric oscillator resonates at a resonant frequency; and measuring said resonant frequency over a pre-determined time period to determine the density of gas in said high-pressure vessel.

In one embodiment, steps a) and b) are repeated one or more times such that a series of measurements of the gas density within the pressure vessel over a period of time is obtained, said series of measurements being utilised to determine the change in mass of gas within pressure vessel during said period of time.

In one embodiment, said piezoelectric oscillator comprises a quartz crystal oscillator.

In an embodiment, the quartz crystal comprises at least one tine. In a variation, the quartz crystal comprises a pair of planar tines.

In an embodiment, the quartz crystal is AT cut or SC cut.

In a variation, the surface of the quartz crystal is directly exposed to the gas.

In one embodiment, the sensor assembly comprises a drive circuit. In a variation, the sensor assembly comprises a drive circuit comprising a Darlington pair arranged in a feedback configuration from a common emitter amplifier.

In one embodiment, the sensor assembly comprises a power source. In one arrangement, the power source comprises a lithium-ion battery.

In one embodiment, the sensor assembly comprises a processor.

In one embodiment, the pressure vessel comprises a high pressure vessel. A high pressure vessel is a vessel arranged to withstand internal pressures generally greater than 10 bar.

In a variation, the pressure vessel comprises a gas cylinder.

In a variation, said piezoelectric oscillator comprises a quartz crystal oscillator.

In a variation, the gas is a permanent gas.

In one arrangement, the high-pressure vessel is a gas cylinder.

In an embodiment, the sensor assembly comprises a drive circuit. In an embodiment, the sensor assembly comprises a drive circuit comprising a Darlington pair arranged in a feedback configuration from a common emitter amplifier.

In one embodiment, the sensor assembly comprises a power source. In one arrangement, the power source comprises a lithium-ion battery.

In one embodiment, the sensor assembly comprises a processor.

In one embodiment, the sensor assembly is arranged to drive the piezoelectric oscillator such that the piezoelectric oscillator resonates at a resonant frequency and to measure said resonant frequency over a pre-determined time period to determine the density of gas in said pressure vessel.

In one embodiment, the sensor assembly is further arranged to perform repeat measurements of the mass of the gas within the pressure vessel at discrete time intervals to obtain a plurality of measurements, and to determine, from said plurality of measurements, the mass flow of gas to/from the pressure vessel during the discrete time intervals. more times such that a series of measurements of the gas density within the pressure vessel over a period of time is obtained, said series of measurements being utilised to determine the change in mass of gas within pressure vessel during said period of time.

According to a fourth aspect of the present invention, there is provided a valve arrangement comprising the sensor assembly of the first aspect, the valve arrangement being for connection to a pressure vessel body to form the pressure vessel having a fixed internal volume, the valve arrangement being arranged to enable selective filling of the pressure vessel with gas or dispensation of gas from the pressure vessel.

In one embodiment, the sensor assembly comprises a drive circuit. In one embodiment, the sensor assembly comprises a power source. In a variation, the power source comprises a lithium-ion battery.

In one embodiment, the sensor assembly is located entirely within the fixed internal volume of the pressure vessel.

In one arrangement, the pressure vessel body comprises a gas cylinder.

According to a fifth embodiment of the present invention, there is provided a computer program product executable by a programmable processing apparatus, comprising one or more software portions for performing the steps of the third aspect.

According to a sixth embodiment of the present invention, there is provided a computer usable storage medium having a computer program product according to the fifth aspect stored thereon.

Embodiments of the present invention will now be described in detail with reference to the accompanying drawings, in which:

FIG. 1 shows a schematic view of a gas cylinder assembly 10 according to an embodiment of the invention.

Figure 1:
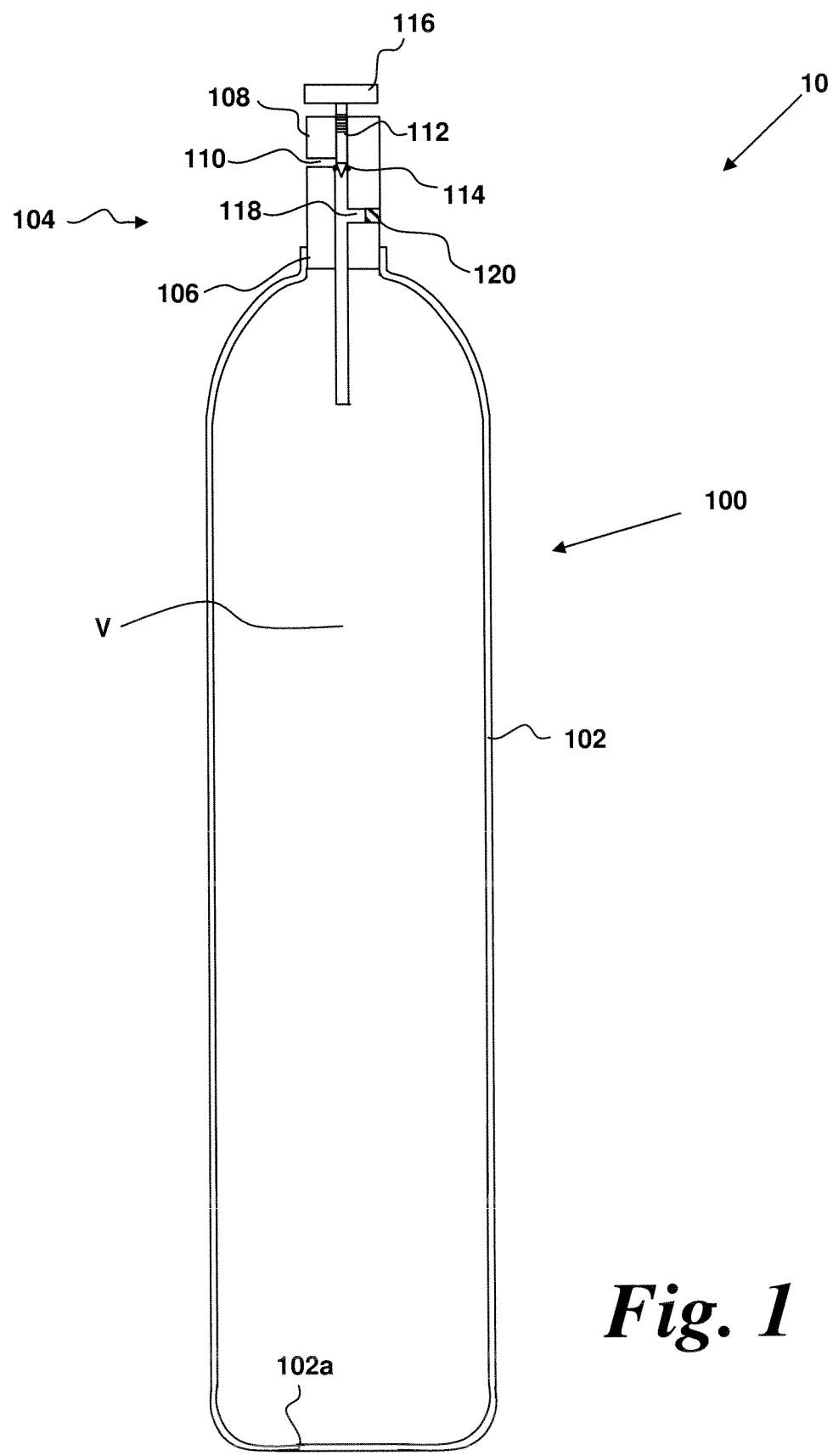
FIG. 1 is a schematic diagram of a gas cylinder assembly.

The gas cylinder assembly 10 comprises a gas cylinder 100 having a gas cylinder body 102 and a valve 104. The gas cylinder body 102 comprises a generally cylindrical container having a flat base 102a arranged to enable the gas cylinder 100 to stand unsupported on a flat surface.

The gas cylinder body 102 is formed from steel, aluminium and/or composite materials and is adapted and arranged to withstand internal pressures up to approximately 900 bar g. An aperture 106 is located at a proximal end of the gas cylinder body 102 opposite to the base 102a and comprises a screw thread (not shown) adapted to receive the valve 104.

The gas cylinder body 102 and valve 104 define a pressure vessel (in this embodiment, in the form of the gas cylinder 100) having an internal volume V. The internal volume V is fixed. By this is meant that the structure of the gas cylinder 100 is such that the internal volume V thereof (and, concomitantly, the volume of a gas contained therein) can be assumed not to vary by a significant degree in use, storage or in dependence upon environmental conditions such as temperature, pressure or humidity. The internal volume V of the gas cylinder 100 is intended to include the entire volume within the gas cylinder body 102 and the valve 104. In other words, the internal volume V is the total internal volume within the gas cylinder assembly 10 where gas is held under pressure.

Any suitable fluid may be contained within the gas cylinder assembly 100. However, the present embodiment relates, but is not exclusively limited to, purified permanent gases which are free from impurities such as dust and/or moisture. Non-exhaustive examples of such gases may be: Oxygen, Nitrogen, Argon, Helium, Hydrogen, Methane, Nitrogen Trifluoride, Carbon Monoxide, Carbon Dioxide, Krypton, Neon or mixtures thereof (for example, Argon and Carbon Dioxide).

The valve 104 comprises a housing 108, an outlet 110, a valve body 112 and a valve seat 114. The housing 108 comprises a complementary screw thread for engagement with the aperture 106 of the gas cylinder body 102. The outlet 110 is adapted and arranged to enable the gas cylinder 100 to be connected to other components in a gas assembly; for example, hoses, pipes, or further pressure valves or regulators. The valve 104 may, optionally, comprise a VIPR (Valve with Integrated Pressure Regulator).

The valve body 112 can be axially adjusted towards or away from the valve seat 114 by means of rotation of a graspable handle 116 selectively to open or to close the outlet 110. In other words, movement of the valve body 112 towards or away from the valve seat 112 selectively controls the area of the communication passageway between the interior of the gas cylinder body 102 and the outlet 110. This, in turn, controls the flow of gas from the interior of the gas cylinder assembly 100 to the external environment.

A through-hole 118 is formed in the housing 108 downstream of the outlet 110. The through-hole 118 is closed by means of a feed through 120 which enables components (such as wires) to be fed through from external of the gas cylinder 100 to the interior of the gas cylinder 100. The feed through 120 functions as a high pressure seal maintaining the integrity of the gas cylinder 100.

Figure 2:
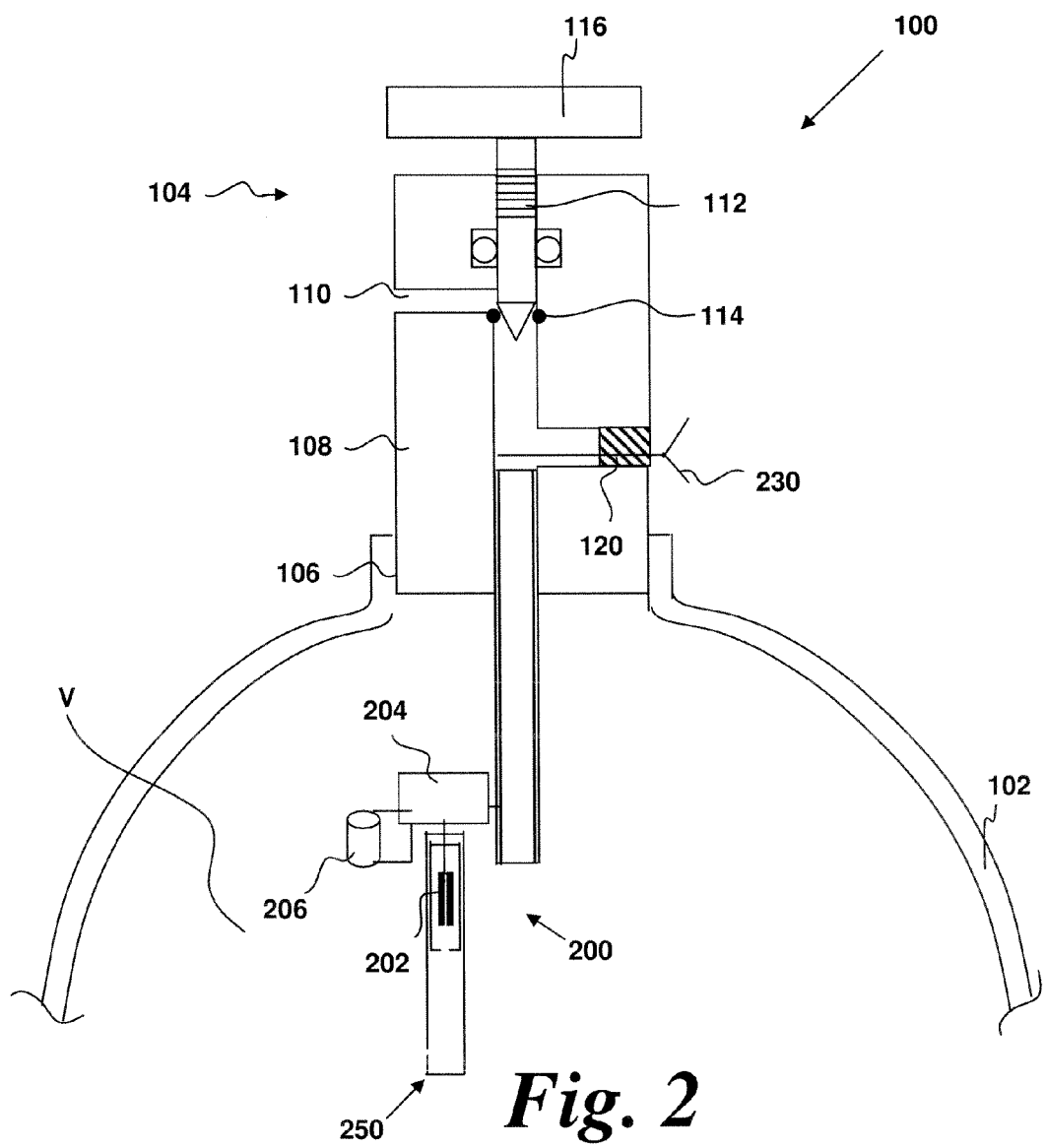
FIG. 2 is a schematic diagram showing an upper part of the gas cylinder assembly according to an embodiment of the invention.

The gas cylinder assembly 10 is provided with a sensor assembly 200. The sensor assembly 200 is arranged to measure the density of the gas within the internal volume V of the gas cylinder 100. The sensor assembly 200 is shown in FIG. 2 and comprises a quartz crystal oscillator 202 connected to a drive circuit 204 and a battery 206 by suitable wiring. A processor 220 (not shown in FIG. 2) may also be provided, either separately or as part of the drive circuit 204. This will be described later.

In the embodiment of FIG. 2, the whole of the sensor assembly 200 is located within the internal volume V of the gas cylinder 100. Therefore, the quartz crystal oscillator 202, the drive circuit 204 (and processor 220, if provided) and the battery 206 are all located within the internal volume V of the gas cylinder 100. The components of the sensor assembly 200 are completely immersed in the gas and are under isostatic gas pressure within the gas cylinder 100. Consequently, the sensor assembly 200 experiences the full gas pressure of the gas within the gas cylinder 100.

As shown in FIG. 2, the sensor assembly 200 may be connected to an antenna 230 for remote communication with, for example, a base station. This will be discussed later. In this case, the antenna 230 may be located outside the gas cylinder 100 and connected to the sensor assembly by means of a wire or equivalent connector. The wire could be passed through the feed through 120 in order to effect a connection between the antenna 230 and the sensor assembly 200.

The antenna 230 itself may be adapted and arranged to use any suitable communication protocol; for example, a non-exhaustive list may be RFID, Bluetooth, Infra red (IR), 802.11 wireless, frequency modulation (FM) transmission or a cell network.

Alternatively, one-wire communication may be implemented. One-wire communication needs only a single metallic conductor to communicate: the 'return' path of the circuit is provided by capacitive coupling through the air between the communicating devices. The skilled person would be readily aware of alternatives of the antenna 230 (and associated transmission hardware) which could be used with the embodiments discussed herein.

The inventors have found that only a few components of the sensor assembly 200 are sensitive to high pressure. In particular, larger components such as batteries can be susceptible to high pressures. However, it has been found that lithium ion batteries perform particularly well under the high pressures encountered within the gas cylinder 100. Consequently, the battery 206 comprises lithium ion cells. However, alternative suitable power sources would be readily be contemplated by the skilled person.

The location of the complete sensor assembly 200 entirely within the gas cylinder 100 provides additional flexibility when configuring gas cylinders 100. In particular, location of relatively fragile electronic components entirely within the strong metal or composite walls of the gas cylinder 100 provides considerable protection from environmental or accidental damage. This is particularly important, for example, in storage areas or depots, where gas cylinders 100 are located adjacent other gas cylinders 100, heavy machinery or rough surfaces.

Further, the location of the electronic components of the sensor assembly entirely within the internal volume V of the gas cylinder 100 enables larger components to be provided which otherwise might not be suitable for use on the external surface of a cylinder 100. For example, a larger battery may be provided in order to increase the operational lifetime of the sensor assembly 200.

Additionally, the internal location of the sensor assembly 200 protects the electronic components from environmental conditions such as salt, water and other contaminants. This would allow, for example, a high impedance circuit which is highly sensitive to salt and water damage to be used as part of the sensor assembly 200.

However, whilst the sensor assembly 200 is shown in FIG. 2 located within the interior of the cylinder, it is to be understood that other locations are suitable. For example, the sensor assembly 200 may be mounted in the valve 104 adjacent the feed through 120 or form a separate section of the valve 104. What is important is that the quartz crystal oscillator 202 is exposed to the gas in the internal volume V of the gas cylinder 100.

Additional variations are within the scope of the present invention. For example, the quartz crystal oscillator 202 may be located within the internal volume V of the gas cylinder 100 and the drive circuit 204 located outside the gas cylinder 100. Consequently, at least a part of the sensor assembly 200 is located in the through-hole 118. The quartz crystal oscillator 202 and the drive circuit 204 are then connected by the wiring 208 which passes through the high pressure feed through 120.

In a further variation, other parts of the sensor assembly may be located within the internal volume V of the gas cylinder 100 and a part may be located externally thereof. For example, the drive circuit 212 and processor 220 may be located within the gas cylinder 100 whilst the battery 206 may be located outside the gas cylinder 100. This arrangement enables the more fragile components of the sensor assembly to be protected from damage and contaminants, whilst the battery 206 is readily accessible for maintenance and replacement.

With regard to external communication, in one configuration, an external aerial or antenna (such as antenna 230) is not explicitly required. For example, communication may be effected by means of acoustic transmission from within the cylinder 100. Acoustic transmission may be effected by a transmitter located within the gas cylinder 100. The transmitter may comprise, for example, a simple fixed-frequency piezoelectric resonator.

A complementary receiver is also required and this component may be located remote from the cylinder 100 and may comprise hardware such as, for example, a phase-locked loop tone detector integrated with a microphone. Such an acoustic arrangement provides the advantage that no feed-through is required (as is the case for the antenna 230) and that all of the electronic components can be located entirely within the cylinder 100.

Alternatively, the sensor assembly 200 may be connected to a display device (not shown) mounted on the gas cylinder itself. This may take the form of a digital display which is operable to display the mass of gas remaining in the cylinder 100 or, for example, the rate of usage of gas.

In this arrangement, the quartz crystal oscillator 202 is constantly under isostatic pressure within the internal volume V of the gas cylinder 100 and, consequently, does not experience a pressure gradient. In other words, any mechanical stress originating from the pressure difference between the internal volume V of the gas cylinder 100 and the external environment is across the feed through 120.

The benefits of internal location of the sensor assembly 200 are unique to solid state sensor devices such as the quartz crystal oscillator 202. For example, a conventional pressure sensor such as a Bourdon gauge cannot be located in this manner. Whilst a crystal-based sensor can operate totally immersed in gas at constant pressure, a conventional pressure sensor is unable to measure isostatic pressure and requires a pressure gradient in order to function. Consequently, a conventional pressure gauge must be located between the high pressure to be measured and the atmosphere. This precludes the location of a conventional pressure gauge entirely within a gas cylinder 100.

The sensor assembly 200 will now be described in more detail with reference to FIGS. 2 and 3a to 3f. The quartz crystal oscillator 202 comprises a small, thin section of cut quartz. Quartz demonstrates piezoelectric behaviour, i.e. the application of a voltage across the crystal causes the crystal to change shape, generating a mechanical force. Conversely, a mechanical force applied to the crystal produces an electrical charge.

Two parallel surfaces of the quartz crystal oscillator 202 are metallised in order to provide electrical connections across the bulk crystal. When a voltage is applied across the crystal by means of the metal contacts, the crystal changes shape. By application of an alternating voltage to the crystal, the crystal can be caused to oscillate.

The physical size and thickness of the quartz crystal determines the characteristic or resonant frequency of the quartz crystal. Indeed, the characteristic or resonant frequency of the crystal 202 is inversely proportional to the physical thickness between the two metallised surfaces.

The resonant vibration frequency of a quartz crystal will vary depending upon the environment in which the crystal is located. In a vacuum, the crystal will have a particular frequency. However, this frequency will change in different environments. For example, in a fluid, the vibration of the crystal will be damped by the surrounding molecules of the fluid and this will affect the resonant frequency and the energy required to oscillate the crystal at a given amplitude.

Further, adsorption of gas or deposition of surrounding materials onto the crystal will affect the mass of the vibrating crystal, altering the resonant frequency. This forms the basis for commonly used selective gas analysers in which an absorbing layer is formed on the crystal and increases in mass as gas is absorbed onto the absorbing layer. However, in the present case, no coating is applied to the quartz crystal oscillator 202. Indeed, adsorption or deposition of material onto the quartz crystal oscillator 202 is undesirable in the present case since the accuracy of the measurement may be affected.

The quartz crystal oscillator 202 of the present embodiment is tuning fork-shaped and comprises a pair of tines 202a (FIG. 3a) approximately 5 mm long arranged to oscillate, in this embodiment, at a resonant frequency of 32.768 kHz. The tines 202a of the fork oscillate normally in their fundamental mode, in which they move synchronously towards and away from each other at the resonant frequency.

Additionally, it is desirable to use quartz which is AT cut or SC cut. In other words, a planar section of quartz is cut at particular selected angles so that the temperature coefficient of the oscillation frequency can be arranged to be parabolic with a wide peak around room temperature. Therefore, the crystal oscillator can be arranged such that the slope at top of the peak is precisely zero.

Such crystals are commonly available at relative low cost. In contrast to the majority of quartz crystal oscillators which are used in vacuo, in the present embodiment the quartz crystal oscillator 202 is exposed to the gas under pressure in the internal volume V of the gas cylinder 100.

The sensor assembly 200 further comprises a housing 250. The housing 250 is operable to enclose the quartz crystal oscillator 202 and, in use, is located in the internal volume V of the gas cylinder 100. The housing 250 is operable to reduce the effect of convection currents within the gas cylinder 100 on measurements made by the sensor assembly 200. The housing 250 of FIG. 2 is shown in more detail in FIG. 3a.

Figure 3A:
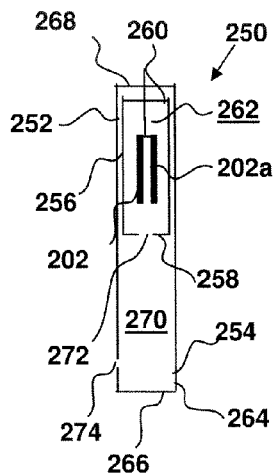
FIG. 3a is a schematic diagram showing the housing of the sensor assembly of the embodiment of FIG. 2.

With reference to FIG. 3a, the housing 250 comprises, in this embodiment, a first housing portion 252 and a second housing portion 254. The first housing portion 252 has a substantially cylindrical side wall 256, a distal end wall 258 and a proximal end wall 260 adjacent the quartz crystal oscillator 202 and which seals the proximal end of the housing 250. The walls of the first housing portion 252 define a first chamber 262. The first chamber 262 substantially encloses the quartz crystal oscillator 202 and is located adjacent the proximal end of the housing 250.

The first housing portion 254 may comprise a conventional pressure housing as commonly available for quartz crystal sensors. This may reduce manufacturing costs. However, alternative configurations may be used, some possible variations of which are illustrated in FIGS. 3b to 3f.

The second housing portion 254 has a substantially cylindrical side wall 264, a distal end wall 266 and a proximal end wall 268. The walls of the second housing portion 254 define a second chamber 270. In this embodiment, the second housing portion 254 is cylindrical with a diameter of approximately 6 mm and a length of approximately 80 mm. However, this is not to be taken as limiting and dimensions and cross-sectional shapes may be varied as required.

The second chamber 270 is located adjacent the first chamber 262 and is in fluid communication therewith by means of a through-hole 272 in the distal end wall 258 of the first housing portion 252. In this embodiment, the through-hole 272 has a diameter of approximately 0.35 mm. However, other shapes and dimensions of through-hole could be used as required. In addition, a plurality of through-holes 272 could be provided if required.

A further through-hole 274 is formed in the side wall 264 of the second housing portion 254 such that the second chamber 270 is in fluid communication with the gas in the interior volume V of the gas cylinder 100 and externally of the housing 250. In this embodiment, the further through-hole 274 has a diameter of 0.22 mm. However, an alternative size of through-hole 274 of 0.35 mm has also been found to yield good results. The skilled person would be readily aware of the configurations, dimensions and shapes of through-hole which could be utilised with the present invention. In addition, a plurality of through-holes 274 could be provided.

The structure of the housing 250 is such that the first and second chambers 262, 270 are in series fluid communication with one another and with the interior volume V of the gas cylinder 100. In other words, the gas to which the quartz crystal oscillator 202 is exposed has to pass from the internal volume V of the gas cylinder 100, through the second chamber 270 to the first chamber 262 before it reaches the quartz crystal oscillator 202.

In the embodiment shown in FIGS. 2 and 3a, the first and second chambers 262, 270 formed by the housing 250 are formed as separate structures. However, this need not be the case and a single common housing 250 may be utilised.

FIGS. 3b through 3f show alternative embodiments of the housing 250 within the scope of the present invention. For clarity, reference numerals referring to features in common with the embodiment of FIG. 3a have been omitted.

Figure 3B:
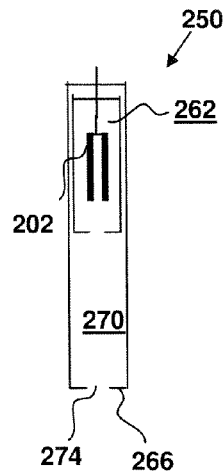
FIGS. 3b to 3f are schematic diagrams showing alternative variations of housing suitable for use with the sensor assembly of the embodiment of FIG. 2.

FIG. 3b shows a second embodiment of the housing 250. The second embodiment is structurally similar to the first embodiment, except that the through-hole 274 is formed in the distal end wall 266 of the second housing portion 254.

Figure 3C:
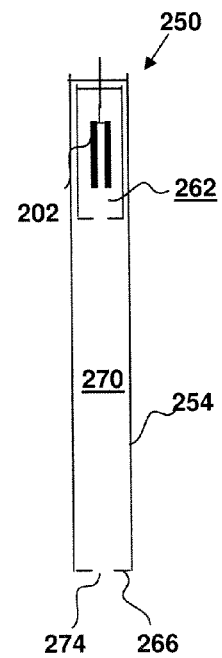

FIG. 3c shows a third embodiment of the housing 250. The embodiment of FIG. 3c is structurally similar to the first and second embodiments of the housing 250 except that the second housing portion 254 has an extended length. In this embodiment, the second housing portion 254 has a length of approximately 230 mm. Whilst FIG. 3c is shown with the through-hole 274 at a distal end, the through-hole 274 could equally be formed in the side wall 264 of the second housing portion 254.

Figure 3D:
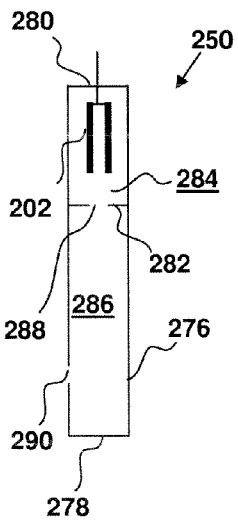
Figure 3E:
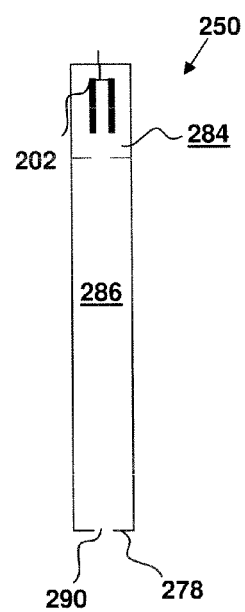
Figure 3F:
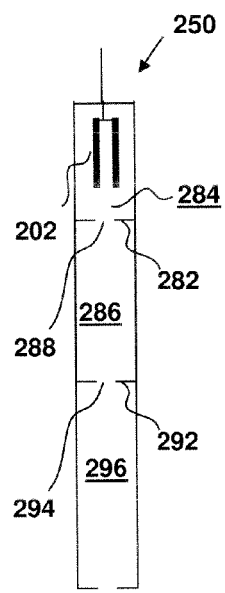

The embodiments of FIGS. 3d to 3f show different structures of the housing 250. The fourth embodiment of the housing 250 shown in FIG. 3d differs from the previous embodiments in that the housing 250 is a unitary member and comprises a cylindrical outer wall 276, a distal end wall 278 and a proximal seal 280.

The walls 276, 278, 280 delimit an interior of the housing 250. The housing 250 further comprises an internal wall 282 which divides the interior of the housing 250 into first and second chambers 284, 286. The first chamber 284 substantially encloses the quartz crystal oscillator 202 and is located adjacent the proximal end of the housing 250.

The second chamber 286 is located adjacent the first chamber 284 and is in fluid communication therewith by means of a through-hole 288 in the internal wall 282. In this embodiment, the through-hole 288 has a diameter of approximately 0.35 mm. However, other shapes and dimensions of through-hole could be used as required. In addition, a plurality of through-holes 288 could be provided if required.

A further through-hole 290 is provided to enable fluid communication between the second chamber 286 and the internal volume V of the gas cylinder 100. In common with the first embodiment, the through-hole 290 is provided in the side wall 276 of the housing 250.

A fifth embodiment of the housing 250 is shown in FIG. 3e. The fifth embodiment of the housing 250 is structurally similar to the fourth embodiment; however, the through-hole 290 is provided in the distal end wall 278 of the housing 250 and the housing 250 has a greater length (in this embodiment, 230 mm) such that the second chamber 286 has a greater internal volume. Either of these variations could be applied to the fifth embodiment.

A sixth embodiment of the housing 250 is shown in FIG. 3f. The sixth embodiment of the housing 250 is structurally similar to the fifth embodiment; however, a second internal wall 292 is provided. The second internal wall 292 has a through-hole 294 formed therein and divides the interior of the housing 250 into three chambers—a first chamber 284, a second chamber 286 and a third chamber 296.

The first, second and third chambers 284, 286, 296 are in series fluid communication with one another and with the interior of the gas cylinder 100 external to the housing 250. In other words, the gas to which the quartz crystal oscillator 202 is exposed has to pass sequentially and consecutively from the internal volume V of the gas cylinder 100, through the third chamber 296, the second chamber 286 to the first chamber 284 before it reaches the quartz crystal oscillator 202.

The provision of a series of chambers as shown in the first to sixth embodiments of the housing 250 described above enables pneumatic damping of the convection currents within the gas cylinder 100. As described above, a result of temperature differences within the cylinder 100 is that convection will often take place in a cylinder. The convection takes place in a turbulent way, with modulations of density and temperature (such that $\rho \sim 1/T$) with almost no resulting change in pressure.

The inventors understand the principle of operation of the housing 250 to be as follows. The housing 250 defines an internal volume of gas which tends to average changes in the density and temperature. In principle, there will be no flow through the through-holes in the housing 250 because of the lack of change in the pressure. Therefore, the system will provide a steady output at a steady pressure as the density and temperature vary just outside it. Only if the temperature of the housing 250 changes will the measured density change. However, this is limited in practice because of the large thermal mass of the volume of gas within the interior of the housing 250.

However, the inventors have found that the housing 250 responds differently with respect to pressure fluctuations seen, for example, when flow is drawn from the gas cylinder 100. In this case, the through-holes are sufficiently large that such the corresponding pressure change is communicated almost instantaneously via fluid flow through the through-holes.

It has been found that, in order to obtain the benefits described above, a housing 250 comprising at least two chambers is required. A single chamber arrangement has been found to be ineffectual in providing sufficient isolation from the density and temperature changes resulting from the convection currents within the cylinder.

Figure 4:
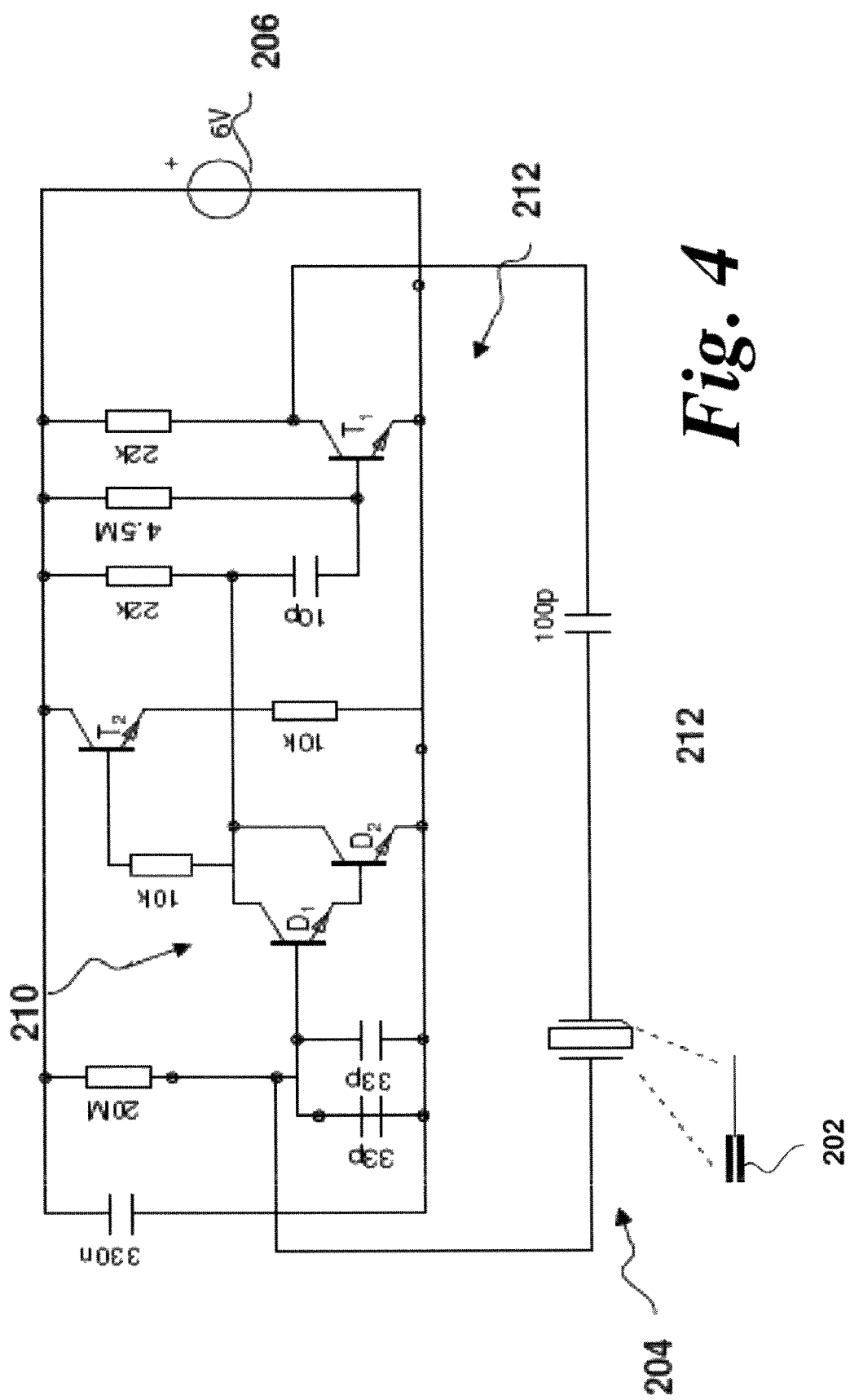
FIG. 4 is a schematic diagram of a drive circuit for use with the embodiments of the invention.

The drive circuit 204 for driving the quartz crystal oscillator 202 is shown in FIG. 4. The drive circuit 204 must meet a number of specific criteria. Firstly, the quartz crystal oscillator 202 of the present invention may be exposed to a range of gas pressures; potentially, the pressures may vary from atmospheric pressure (when the gas cylinder 100 is empty) to around 900 bar g if the gas cylinder contains a pressurised gas such as hydrogen. Thus, the quartz crystal 202 is required to operate (and restart after a period of non-use) under a wide range of pressures.

Consequently, the quality (Q) factor of the quartz crystal oscillator 202 will vary considerably during use. The Q factor is a dimensionless parameter relating to the rate of damping of an oscillator or resonator. Equivalently, it may characterise the bandwidth of a resonator relative to its centre frequency.

In general, the higher the Q factor of an oscillator, the lower the rate of energy loss relative to the stored energy of the oscillator. In other words, the oscillations of a high Q factor oscillator reduce in amplitude more slowly in the absence of an external force. Sinusoidally driven resonators having higher Q factors resonate with greater amplitudes at the resonant frequency but have a smaller bandwidth of frequencies around that frequency for which they resonate.

The drive circuit 204 must be able to drive the quartz crystal oscillator 202 despite the changing Q factor. As the pressure in the gas cylinder 100 increases, the oscillation of the quartz crystal oscillator 202 will become increasingly damped, and the Q factor will fall. The falling Q factor requires a higher gain to be provided by an amplifier in the drive circuit 204. However, if too high an amplification is provided, the drive circuit 204, the response from the quartz crystal oscillator 202 may become difficult to distinguish. In this case, the drive circuit 204 may simply oscillate at an unrelated frequency, or at the frequency of a non-fundamental mode of the quartz crystal oscillator 202.

As a further limitation, the drive circuit 204 must be low power in order to run on small low power batteries for a long time with or without supplementary power such as photovoltaic cells.

The drive circuit 204 will now be described with reference to FIG. 4. In order to drive the quartz crystal oscillator 202, the drive circuit 204 essentially takes a voltage signal from the quartz crystal oscillator 202, amplifies it, and feeds that signal it back to the quartz crystal oscillator 202. The fundamental resonant frequency of the quartz crystal oscillator 202 is, in essence, a function of the rate of expansion and contraction of the quartz. This is determined in general by the cut and size of the crystal.

However, external factors also affect the resonant frequency. When the energy of the generated output frequencies matches the losses in the circuit, an oscillation can be sustained. The drive circuit 204 is arranged to detect and maintain this oscillation frequency. The frequency can then be measured by the processor 220, used to calculate the appropriate property of the gas required by the user and, if required, output to a suitable display means (as will be described later).

The drive circuit 204 is powered by a 6 V power source 206. The power source 206, in this embodiment, comprises a lithium ion battery. However, alternative power sources will be readily apparent to the person skilled in the art; for example, other battery types both rechargeable and non-rechargeable and a solar cell arrangement.

The drive circuit 204 further comprises a Darlington pair Common Emitter amplifier 210. A Darlington pair comprises a compound structure consisting of two bipolar NPN transistors configured such that the current amplified by a first of the transistor is amplified further by the second one. This configuration enables a higher current gain to be obtained when compared to each transistor being taken separately. Alternative, PNP bipolar transistors may be used.

The Darlington pair 210 is arranged in a feedback configuration from a single transistor ($T_1$) Common Emitter amplifier 212. A NPN bipolar junction transistor is shown in FIG. 4. However, the skilled person would be aware of alternative transistor arrangements which may be used; for example, a bipolar junction PNP transistor or Metal Oxide Semiconductor Field Effect Transistors (MOSFETs).

The drive circuit 204 comprises a further NPN emitter follower transistor $T_2$ which acts as a buffer amplifier 214. The buffer amplifier 214 is arranged to function as a buffer between the circuit and the external environment.

A capacitor 216 is located in series with the quartz crystal oscillator 202. The capacitor 216, in this example, has a value of 100 pF and enables the drive circuit 204 to drive the quartz crystal oscillator 202 in situations where the crystal has become contaminated, for example by salts or other deposited materials.

Figure 5:
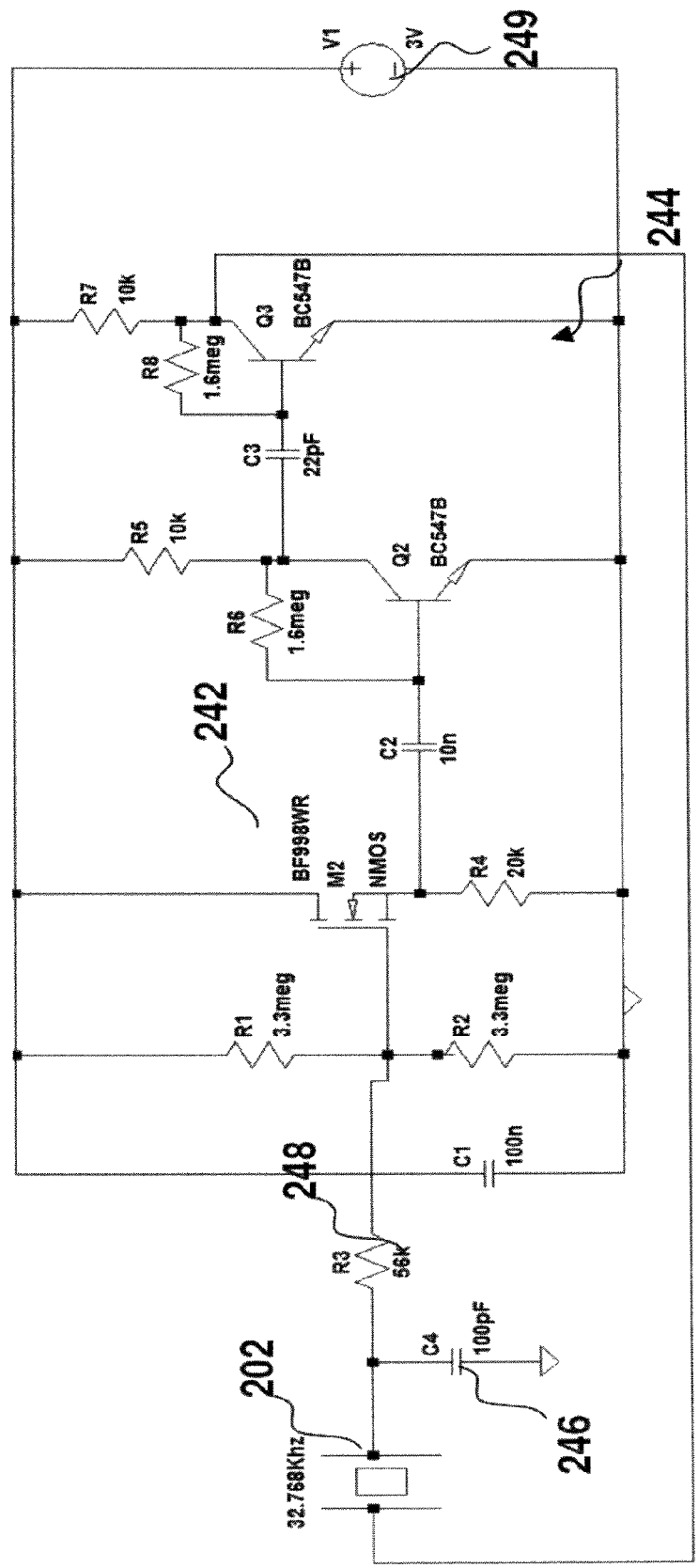
FIG. 5 is a schematic diagram showing an alternative drive circuit for use with the embodiments of the invention.

An alternative drive circuit 240 will now be described with reference to FIG. 5. The drive circuit 240 may be used in place of the drive circuit 204 described above. In contrast to the drive circuit 204 described above, the drive circuit 240 includes a common drain Metal Oxide Semiconductor Field Effect Transistor (MOSFET) amplifier 242 in place of the Darlington pair of the circuit of FIG. 6. The MOSFET 242 functions as a high impedance input which enables the input impedance of the amplifier stage to be matched to the high impedance of the quartz crystal oscillator 202. In other words, the MOSFET 242 provides a unity gain with a high input impedance to reduce the electrical load on the quartz crystal oscillator 202.

The output of the common drain MOSFET amplifier 242 is fed to two successive single transistor (Q2,Q3) Common Emitter Amplifiers 244. Resistors R6 and R8 provide both negative feedback and biasing current for the transistors. The Common Emitter Amplifiers 244 provide a high gain to amplify the oscillations of the quartz crystal oscillator 202 and, in this embodiment, comprise NPN bipolar junction transistors. However, the skilled person would be aware of alternative transistor arrangements which may be used; for example, a bipolar junction PNP transistor or MOSFETs.

A capacitor 246 is connected between the quartz crystal oscillator 202 and ground. The capacitor 246, in this embodiment is operable to increase the drive to the quartz crystal oscillator 202.

A resistor 248 is connected in series with the quartz crystal oscillator 202. The resistor 248, in this embodiment, has a value of 56 kΩ and damps the oscillations of quartz crystal oscillator 202 in order to enable the circuit to oscillate over a wide range of pressures with only gradual changes in waveform.

The drive circuit 240 is powered by a 3 V battery 249. The battery 249, in this embodiment, comprises a lithium battery. However, alternative power sources will be readily apparent to the person skilled in the art; for example, other battery types both rechargeable and non-rechargeable and a solar cell arrangement. Alternatively, a mains supply arrangement may be used after DC rectification and appropriate voltage reduction.

Figure 6:
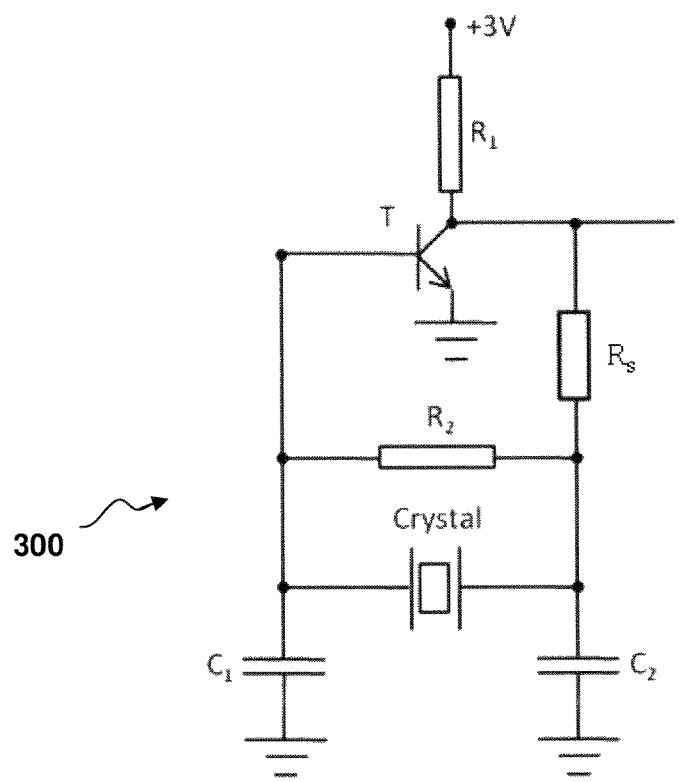
FIG. 6 is a schematic diagram showing a further alternative drive circuit for use with the embodiments of the invention.

A further alternative drive circuit 300 will now be described with reference to FIG. 6. The drive circuit shown in FIG. 6 is configured similarly to a Pierce oscillator. Pierce oscillators are known from digital IC clock oscillators. In essence, the drive circuit 300 comprises a single digital inverter (in the form of a transistor) T, three resistors $R_1$, $R_2$ and $R_S$, two capacitors $C_1$, $C_2$, and the quartz crystal oscillator 202.

In this arrangement, the quartz crystal oscillator 202 functions as a highly selective filter element. Resistor $R_1$ acts as a load resistor for the transistor T. Resistor $R_2$ acts as a feedback resistor, biasing the inverter T in its linear region of operation. This effectively enables the inverter T to operate as a high gain inverting amplifier. Another resistor $R_S$ is used between the output of the inverter T and the quartz crystal oscillator 202 to limit the gain and to dampen undesired oscillations in the circuit.

The quartz crystal resonator 202, in combination with $C_1$ and $C_2$ forms a Pi network band-pass filter. This enables a 180 degree phase shift and a voltage gain from the output to input at approximately the resonant frequency of the quartz crystal oscillator. The above described drive circuit 300 is reliable and cheap to manufacture since it comprises relatively few components.

As discussed above, the sensor assembly 200 may include a processor 220 which receives inputs from the quartz crystal oscillator 202 and drive circuit 204. The processor 220 may comprise and suitable arrangement, such as an Application Specific Integrated Circuit (ASIC) or Field Programmable Gate Array (FPGA). The processor 220 is programmed to calculate, display and communicate parameters useful to users of the cylinder 100.

When used with the quartz crystal oscillator 202, the processor 220 may be configured to measure the frequency f or period of the signal from the drive circuit 204. This may be achieved by, for example, counting oscillations over a fixed time, and convert that frequency into a density value using an algorithm or look-up table. This value is passed to the processor 220 which is configured to perform, based on the supplied inputs, a calculation to determine the mass of the gas in the gas cylinder 100.

The processor 220 may, optionally, be designed for mass production to be identical in all cylinders, with different features in the software and hardware enabled for different gases.

Additionally, the processor 220 may also be configured to minimise power consumption through implementation of standby or "sleep" modes which may cover the processor 220 and additional components such as the drive circuit 204 and quartz crystal oscillator 202.

Various schemes may be implemented; for example, the processor 220 may be on standby for 10 seconds out of every 11 seconds. Further, the processor 220 may control the quartz crystal oscillator 202 and drive circuit 204 such that these components are put on standby for he majority of time, only being switching the more power hungry components on for ½ second every 30 seconds. Alternatively or additionally, communication components such as the antenna 230 can be switched off as required or used to activate the sensor assembly 200.

The theory and operation of the sensor assembly 200 will now be described with reference to FIGS. 7 to 14.

The quartz crystal oscillator 210 has a resonant frequency which is dependent upon the density of the fluid in which it is located. Exposing an oscillating tuning fork-type planar crystal oscillator to a gas leads to a shift and damping of the resonant frequency of the crystal (when compared to the resonant frequency of the crystal in a vacuum). There are a number of reasons for this. Whilst there is a damping effect of the gas on the oscillations of the crystal, the gas adjacent the vibrating tines 210a of the tuning fork crystal oscillator 210 increases the effective mass of the oscillator. This leads to a reduction in the resonant frequency of the quartz crystal oscillator according to the motion of a one-sided, fixed elastic beam:

$$f = \frac{f_0}{\sqrt{1 + \frac{\rho}{M_0}}} \quad 1)$$

Where f is the frequency of oscillation, $f_0$ is the frequency of oscillation in a vacuum, $\rho$ is the gas density, and $M_0$ is a constant.

The density $\rho$ will in almost all cases be small compared to $M_0$, so that the formula can be approximated by the linear equation:

$$f = f_0\left(1 - \frac{\rho}{2M_0}\right) \quad 2)$$

which can re-expressed in terms of the frequency deviation $\Delta f$ from $f_0$ as set out in equation 3):

$$\Delta f = \frac{1}{2}\left(\frac{f_0}{M_0}\right)\rho \quad 3)$$

Figure 7:
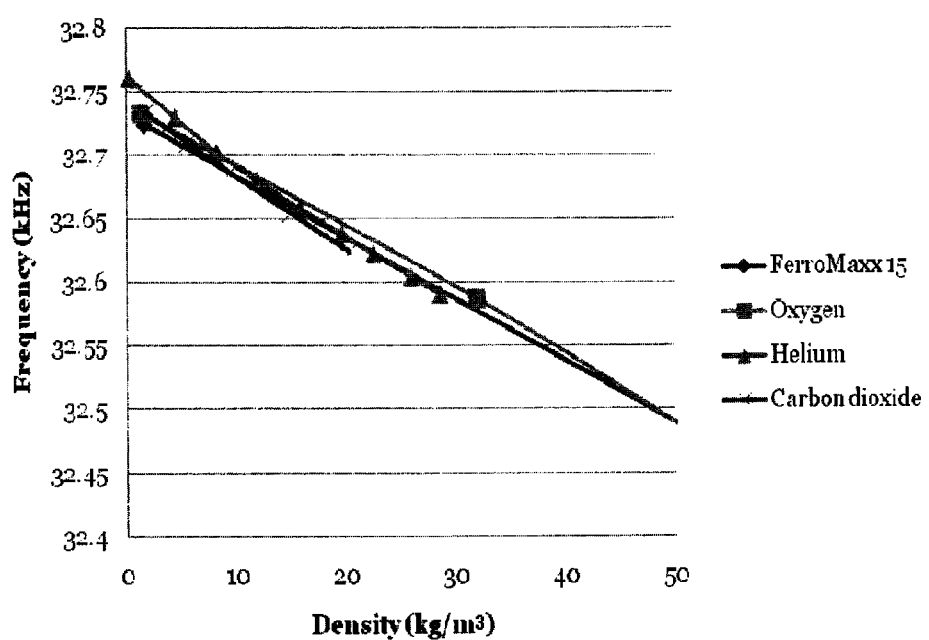
FIG. 7 shows a graph of quartz crystal frequency (kHz) on the Y-axis as a function of density (kg/m$^3$) for a number of different gases.

Consequently, to a good approximation, the change in frequency is proportional to the change in density of the gas to which the quartz crystal oscillator is exposed. FIG. 7 shows, for a number of different gases/gas mixtures, that the resonant frequency of the quartz crystal oscillator 210 varies linearly as a function of density.

In general, the sensitivity of the quartz crystal oscillator 202 is that a 5% change in frequency is seen with, for example, Oxygen gas (having Atomic mass number 32) at 250 bar when compared to atmospheric pressure. Such pressures and gas densities is typical of the storage cylinders used for permanent gases, which are normally between 137 and 450 bar g for most gases, and up to 700 or 900 bar g for helium and hydrogen.

The quartz crystal oscillator 202 is particularly suitable for use as a density sensor for commercially-supplied gases. Firstly, in order to sense accurately the density of a gas, it is necessary for the gas to be free from dust and droplets of liquids, which is guaranteed with commercially supplied gases, but not with air or in the generality of pressure monitoring situations.

Secondly, because the gas pressure within a cylinder can only change slowly during normal use (i.e. as gas is exhausted through the outlet 110), the fact that the quartz crystal oscillator 202 takes a small amount of time (approximately 1 second) to take a reading does not impact the accuracy of measurement. The time period of approximately 1 s is required because of the need to count oscillations and because of the need for the quartz crystal oscillator 202 to reach equilibrium at a new gas pressure.

This method may be less accurate if the gas in the gas cylinder 100 is not uniform—for example, if the gas is a non-uniform mixture such as may occur within a partially liquid-filled cylinder or in the case of a recently prepared and insufficiently mixed mixture of light and heavy gases. However, this is unlikely to occur in most packaged gas applications.

As previously described, the internal volume V of gas within the gas cylinder 100 is fixed. Therefore, once the density $\rho$ of the gas within the internal volume V of the gas cylinder 100 has been obtained from measurement by the sensor assembly 200, the mass M of the gas in the cylinder can be obtained from the following equation:

$$M = \rho V \quad 4)$$

The direct measurement of the density $\rho$ of the gas, therefore, enables the calculation of the mass of gas remaining in the gas cylinder 100.

Measurement of the mass of gas in this way has a number of advantages over known arrangements. For example, the mass measured according to an embodiment of the invention is corrected intrinsically for temperature. In contrast, the measurement of pressure using, for example, a Bourdon gauge varies proportionally with absolute temperature. Therefore, the present arrangement does not require temperature measurement and/or correction as is the case with known arrangements.

Further, the mass of gas measured according to an embodiment of the present invention is intrinsically corrected for compressibility Z. In a conventional arrangement, for example, utilising a Bourdon gauge in order to obtain gas contents from pressure, the compressibility of the gas needs to be corrected for. This is particularly important at high pressures, where the compressibility Z is not proportional to the gas pressure in the way expected of an ideal gas.

Figure 8:
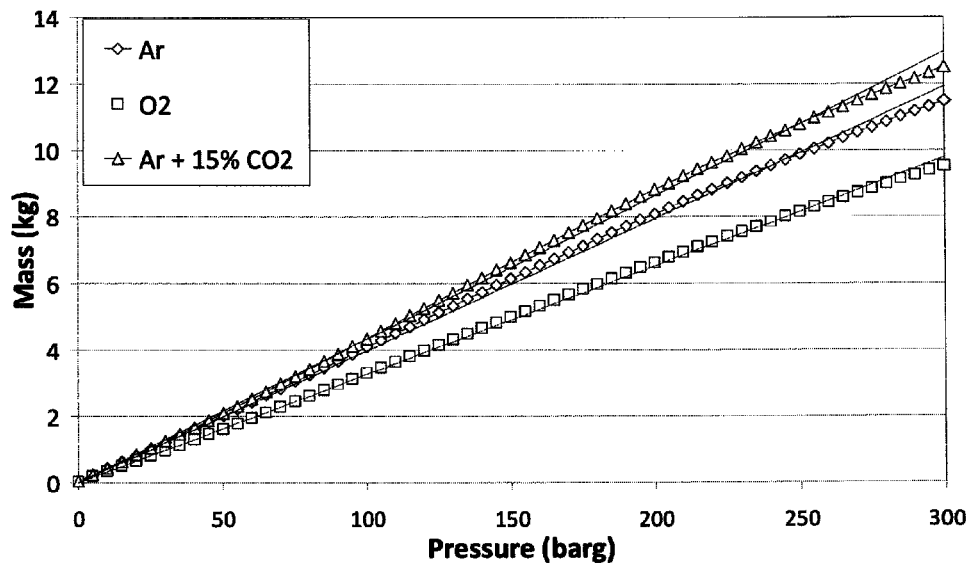
FIG. 8 shows a graph of gas mass (in kg) on the Y-axis as a function of pressure (bar g) on the X-axis for Argon, Oxygen and an Argon:Carbon Dioxide mixture.

The automatic compensation for compressibility is illustrated with reference to FIGS. 8 and 9. FIG. 8 shows a graph of gas mass (in kg) on the Y-axis as a function of Pressure (bar g) for Argon, Oxygen and an Argon: Carbon Dioxide mixture. As shown in FIG. 8, the masses of the different gases vary with increasing pressure. Further, at high pressures in excess of 250 bar g, there is no longer a linear relationship between mass and pressure.

Figure 9:
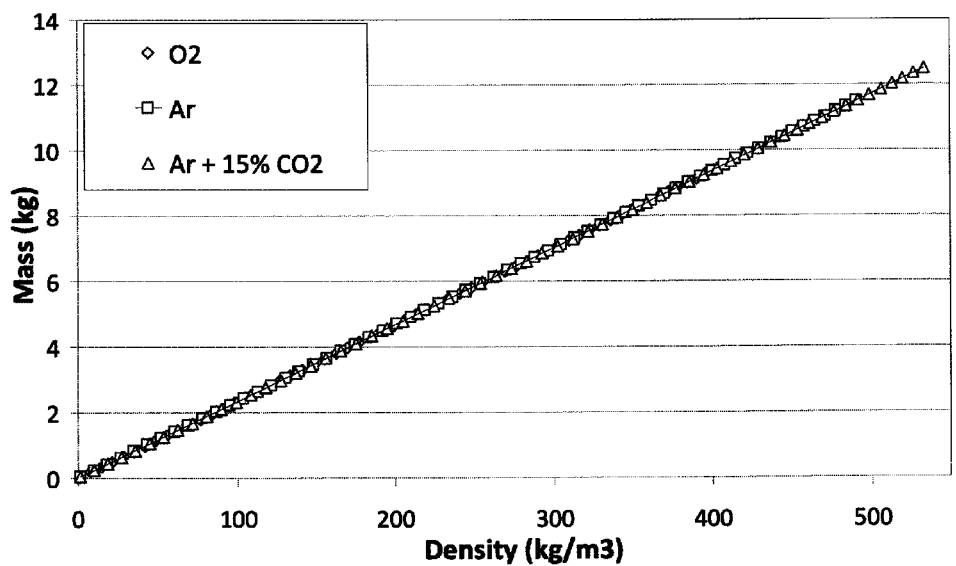
FIG. 9 shows a graph of gas mass (in kg) on the Y-axis as a function of density (in kg/m$^3$) on the X-axis for the same three gases (Argon, Oxygen and an Argon:Carbon Dioxide mixture) as shown in FIG. 7.

FIG. 9 shows a graph of gas mass (in kg) on the Y-axis as a function of Density (in kg/m$^3$) for the same three gases (Argon, Oxygen and an Argon: Carbon Dioxide mixture) as FIG. 8. In contrast to FIG. 8, it can be seen that the mass of gas as a function of density is identical for each gas/gas mixture. Further, the relationship is still linear at high densities. Consequently, the quartz crystal oscillator 202 can be both high resolution and highly linear with density.

As outlined above, the arrangement of the present invention enables mass measurement to very high accuracy with a resolution of parts per million. Coupled with the linear response of the quartz density sensor 202 at high densities and pressures (as illustrated in FIGS. 8 and 9), the high accuracy enables very light gases such as $H_2$ and He to be measured accurately.

In many practical situations, the measurement of mass flow into or from the gas cylinder 100 is important. This may be useful in situations where the usage rate of gas from the gas cylinder 100 is required, for example to calculate the time remaining before the cylinder is emptied. Alternatively or additionally, the mass flow can be monitored in order to administer precise quantities of gas.

Gas density at atmospheric pressure is only on the order of 1 g/liter, and normal gas usage rates are often just a few liters per minute. The inventors have found that the quartz crystal oscillator 202 is sufficiently stable and accurate to enable mass flow of gas exiting the gas cylinder 100 in to be measured by means of the changing density indicated. The mass flow $$\frac{\partial M}{\partial t}$$

is calculated from equation 5):

$$\frac{\partial M}{\partial t} = V \frac{\Delta \rho}{\Delta t} \quad 5)$$

where V is the volume, $\Delta \rho$ the change in density indicated over time interval $\Delta t$. In this instance, the operation of the sensor assembly 200 requires the drive circuit 204 to integrate over a number of oscillation cycles of the quartz crystal oscillator 202.

Therefore, it is not possible to obtain an instantaneous rate of change of density with time, $$\frac{\partial \rho}{\partial t}.$$

However, the rate of change of density with time is relatively low in a gas cylinder 100 under normal operation. Therefore, the measurement taken using the sensor assembly 200 is sufficiently accurate in normal use.

Figure 10:
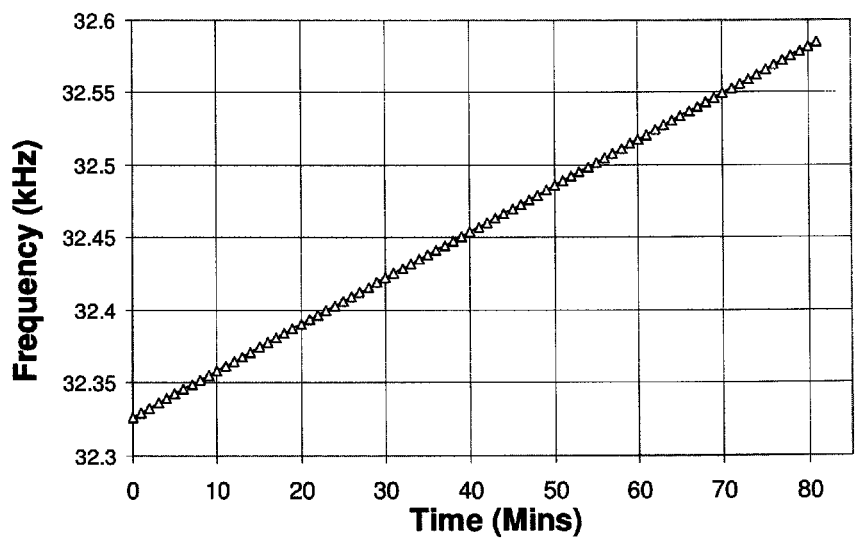
FIG. 10 shows a graph of frequency (in kHz) on the Y-axis as a function of time (in minutes) on the X-axis for a flow rate of 12 l/min from a 50 liter gas cylinder at a pressure of 100 bar g.
Figure 11:
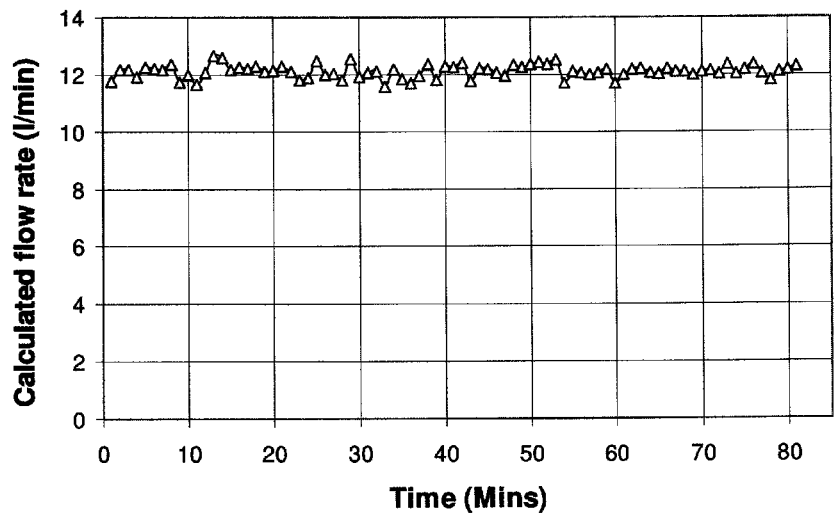
FIG. 11 shows a graph of the calculated flow rate (in liters per minute) on the Y-axis as a function of time (in minutes) on the X-axis for the 50 liter cylinder at a pressure of 100 bar g.

FIGS. 10 and 11 illustrate experimental data of mass flow detection. FIG. 10 shows a graph of frequency (kHz) on the Y-axis as a function of time (in minutes) on the X-axis for a 12 liter per minute flow rate from a 50 liter cylinder at ~100 bar pressure indicated. FIG. 11 shows a graph of the calculated flow rate (in liters per minute) on the Y-axis as a function of time (in minutes) on the X-axis for the 50 liter cylinder at ~100 bar pressure.

These figures illustrate that, for most normal uses, the mass flow rate of gas from a gas cylinder 100 can be determined from a measurement of change of density with time. Consequently, the mass flow rate can be calculated with sufficient accuracy and time resolution using the quartz crystal oscillator 202 and drive circuit 204.

Figure 12:
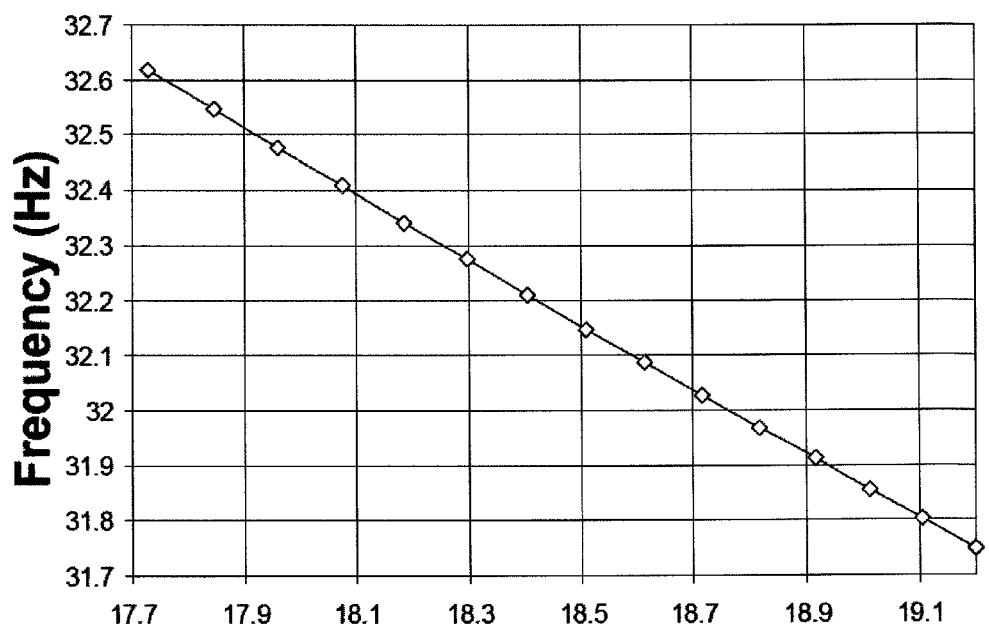
FIG. 12 shows a graph of frequency (in kHz) on the Y-axis as a function of gas cylinder mass (in kg) on the X-axis for a typical gas cylinder.

FIG. 12 illustrates further experimental data showing the operation of the present invention. FIG. 12 shows a graph of frequency (in kHz) on the Y-axis as a function of total cylinder mass (in kg) on the X-axis. As can be seen, the graph is, to a high degree of accuracy, approximately linear. Therefore, FIG. 12 shows that the mass of gas within the gas cylinder 100 can be measured accurately with the quartz crystal oscillator 202.

Figure 13:
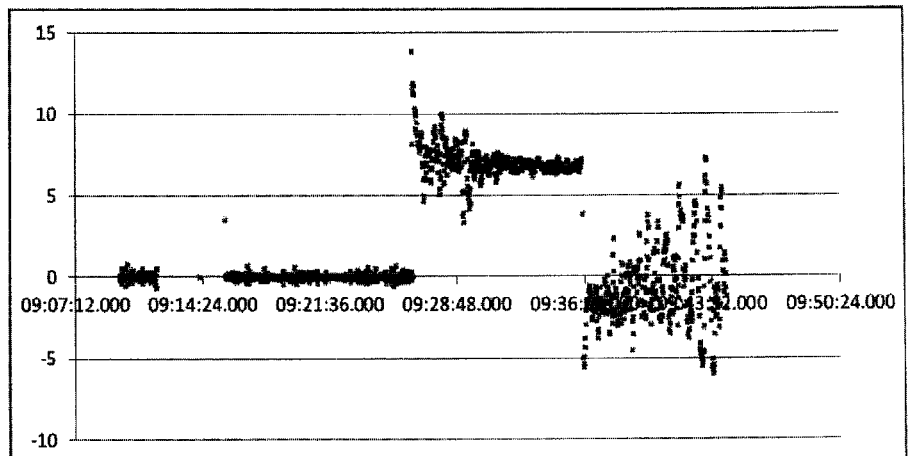
FIG. 13 is a graph of flow rate (in liters/minute divided by two) as a function of time (on the X-axis) in seconds for a flow rate measurement utilising a quartz crystal oscillator without a housing.

However, as described above, when flow is drawn from a cylinder, the top of the cylinder can become significantly colder than the remainder of the cylinder, setting up strong convection currents within the cylinder. FIG. 13 shows the effect of convection on the measurement of gas flow from a cylinder from which a gas flow has been drawn for 10 minutes.

In the experimental set up, the housing 250 is omitted and the quartz crystal oscillator 202 is located in the interior of the gas cylinder 100 uncovered and directly exposed to the gas in the cylinder 100.

It can be seen from FIG. 13 that convection currents cause considerable noise to the flow signal after the flow stops. The Y-axis shows flow in liters/min divided by 2, while the X-axis is time, with one data point per second. The noise level due to convection means that the erroneous flow rates may be detected and little meaningful information can be gathered. In particular, the noise fluctuations may lead to erroneous measurements of flow rates oscillating between +10 liters/min and −10 liters/minute. This is clearly unacceptable for accurate commercial use.

Figure 14:
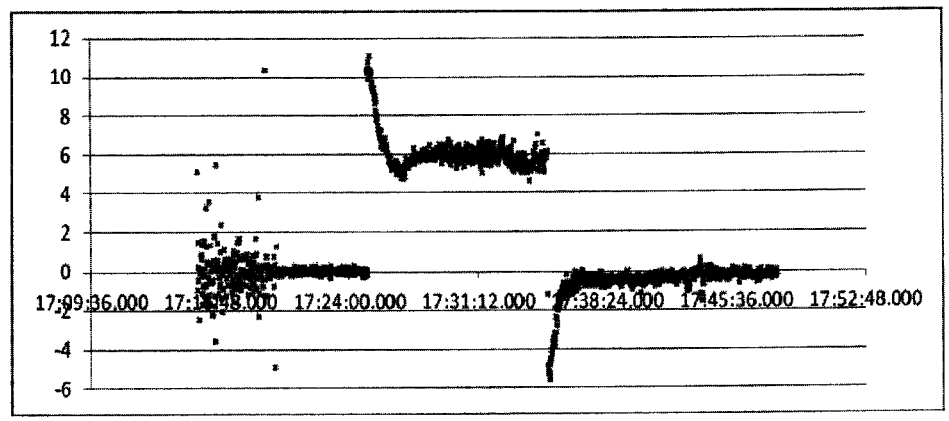
FIG. 14 is a graph of flow rate (in liters/minute divided by two) as a function of time (on the X-axis) in seconds for a flow rate measurement utilising a quartz crystal oscillator surrounded by a housing according to the first embodiment.

FIG. 14 illustrates a similar measurement. However, in this case, the experimental arrangement comprises the housing 250 of the first embodiment which is located around the quartz crystal oscillator 202 to act as a pneumatic damper. As shown in FIG. 14, the data exhibits significantly less noise than the measurement shown in FIG. 13, both when the valve is open and the gas is flowing (at a flow rate of approximately 12 liters/minute) and when the valve is closed.

As shown, a housing 250 according to an embodiment of the present invention significantly reduces the data noise (and resulting measurement errors) due to convection within a cylinder 100.

The inventors have found that this reduction in noise cannot be achieved effectively using electronic filtering alone. For example, whilst applying an RC filter or an exponential digital filter does result in some smoothing of the signal, it has been found experimentally that, in order to obtain acceptable results, a time constant of approximately 30 seconds is required. This slow response time is unacceptable for most typical commercial applications.

However, it has been found that the combination of the housing 250 (which significantly reduces noise due to convection) and electronic filtering can provide good results. Since the noise is significantly reduced by use of the housing 250, electronic filtering can be provided which averages over a shorter time period, improving the response.

An exponential averaging model was applied, utilising the formula of equation 6):

$$\frac{\partial f}{\partial t_{Av}} = \left(\frac{\partial f}{\partial t_{previous}} \times \gamma\right) + \left(\frac{\partial f}{\partial t_{current}} \times (1-\gamma)\right) \quad (6)$$

where $\frac{\partial f}{\partial t_{previous}}$ is the previously calculated value of $\frac{\partial f}{\partial t_{Av}}$ (or the average value), $\frac{\partial f}{\partial t_{current}}$ is the currently recorded $\frac{\partial f}{\partial t}$ value and γ is an exponential decay constant (0 to <1).

However, exponential filtering introduces a time lag to the reported values. This delay can be calculated using equation 7):

$$t_{delay} = \left(\frac{1}{1-\gamma}\right) \times \partial t \quad (7)$$

where ∂t is the time period between readings.

Figure 15:
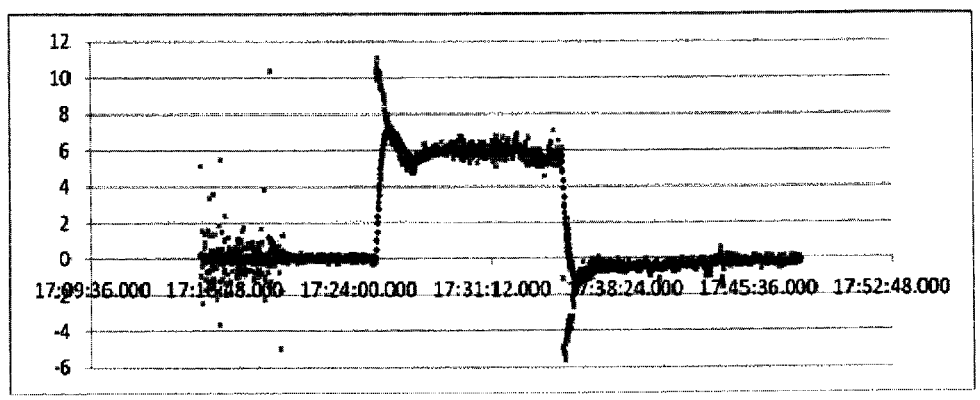
FIG. 15 is a graph of flow rate (in liters/minute divided by two) as a function of time (on the X-axis) in seconds for a flow rate measurement utilising a quartz crystal oscillator surrounded by a housing according to the first embodiment (squares) and for the same data passed through a numerical filter (diamonds)

FIG. 15 shows an experimental measurement showing the effect of filtering with a decay constant γ of 0.9. It can clearly be seen that the filter has the effect of further smoothing the noise of the signal.

Table 1 below shows a summary of measurements made on arrangements of housing according to embodiments of the present invention. As shown below, the use of the various embodiments of the housing 250 result in up to an order of magnitude improvement in noise reduction as a result of convection currents within the cylinder 100. Further, numerical filtering can reduce the flow spread (i.e. the measured variation in flow as a result of noise on the measurement signal) even further. However, the numerical average comes at the cost of response time. Therefore, a trade-off is required in practice.

TABLE 1

| Hardware Type | Total Spread (Hz/s) | Flow Spread (Hz/s) | Flow Spread (equated) (L/min) | Settling Time Start (s) | Settling Time Stop (s) |
| --- | --- | --- | --- | --- | --- |
| No housing | 0.84 | 0.205 | 39 | 23 | >200 |
| 80 mm housing, 0.35 mm through-hole | 0.29 | 0.029 | 5 | 89 | 115 |
| 80 mm housing, 0.22 mm through-hole | 0.30 | 0.023 | 4 | 94 | 126 |
| 230 mm housing, 0.22 mm through-hole | 0.33 | 0.078 | 15 | 84 | 105 |
| 80 mm housing, 0.22 mm through-hole, Numerical Filtering (γ = 0.9) | 0.26 | 0.0085 | 1.6 | 89 | 115 |

Figure 16:
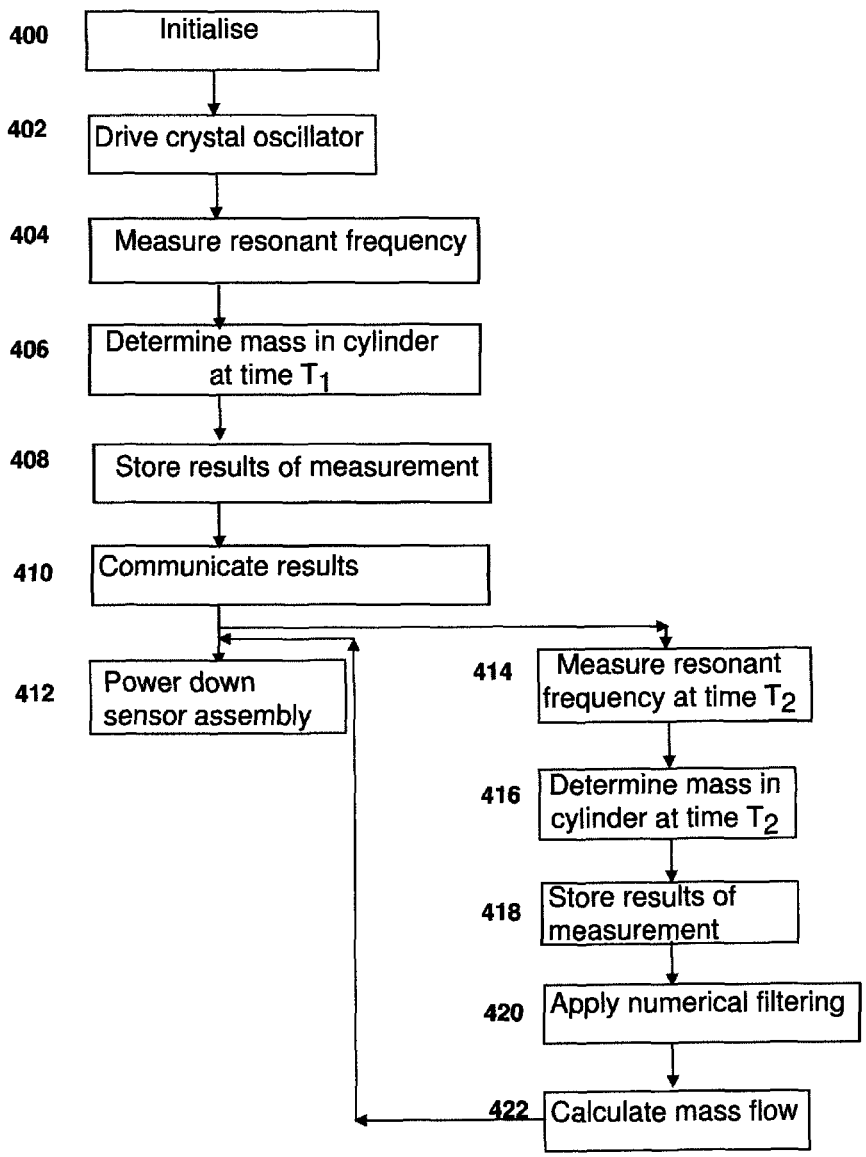
FIG. 16 is a flow chart illustrating a method according to a described embodiment.

A method according to an embodiment of the present invention will now be described with reference to FIG. 16. The method described below is applicable each of the embodiments described above.

Step 400: Initialise Measurement

At step 400, the measurement of the mass of gas in the gas cylinder 100 is initialised. This may be activated by, for example, a user pressing a button on the outside of the gas cylinder 100. Alternatively, the measurement may be initiated by means of a remote connection, for example, a signal transmitted across a wireless network and received by the sensor assembly 200 through the antenna 230 (see FIG. 2).

As a further alternative or addition, the sensor assembly 200 may be configured to initialise remotely or on a timer. The method proceeds to step 402.

Step 402: Drive the Quartz Crystal Oscillator

Once initialised, the drive circuit 204 is used to drive the quartz crystal oscillator 202. During initialisation, the drive circuit 204 applies a random noise AC voltage across the crystal 202. At least a portion of that random voltage will be at a suitable frequency to cause the crystal 202 to oscillate. The crystal 202 will then begin to oscillate in synchrony with that signal.

By means of the piezoelectric effect, the motion of the quartz crystal oscillator 202 will then generate a voltage in the resonant frequency band of the quartz crystal oscillator 202. The drive circuit 204 then amplifies the signal generated by the quartz crystal oscillator 202, such that the signals generated in the frequency band of the quartz crystal resonator 202 dominate the output of the drive circuit 204. The narrow resonance band of the quartz crystal filters out all the unwanted frequencies and the drive circuit 204 then drives the quartz crystal oscillator 202 at the fundamental resonant frequency f. Once the quartz crystal oscillator 202 has stabilised at a particular resonant frequency, the method proceeds to step 304.

Step 404: Measure Resonant Frequency of Quartz Crystal Oscillator

The resonant frequency f is dependent upon the conditions within the internal volume V of the gas cylinder. In the present embodiment, the change in resonant frequency Δf is proportional in magnitude to the change in density of gas within the gas cylinder 100 and will decrease with increasing density.

In order to make a measurement, the frequency of the quartz crystal oscillator 202 is measured for a period of approximately 1 s. This is to enable the reading to stabilise and for sufficient oscillations to be counted in order to determine an accurate measurement. The measurement of frequency is carried out in the processor 220. The processor 220 may also log the time, $T_1$, when the measurement was started.

The quartz crystal oscillator 202 is located within the housing 250 of one of the previously-described embodiments. Therefore, during the measurement period, the housing 250 shields the quartz crystal oscillator 202 from density and temperature variations due to convection within the cylinder 100. This situation may occur when, for example, gas has been drawn from the cylinder 100 for a predetermined period and the top of the cylinder 100 is cold.

Once the frequency has been measured, the method proceeds to step 406.

Step 406: Determine Mass of Gas in Gas Cylinder

Once the frequency of the quartz crystal oscillator 202 has been measured satisfactorily in step 303, the processor 220 then calculates the mass of gas in the gas cylinder 100.

This is done using equation 5) above where the mass of the gas can be calculated directly from the density determined in step 304 and the known internal volume V of the gas cylinder 100. The method then proceeds to step 408.

Step 408: Store Results of Measurement

Once the mass of gas has been calculated, the mass could be simply recorded in an internal memory associated with the processor 220 of the sensor assembly 200 for later retrieval. As a yet further alternative, the mass of gas at time $T_1$ could be stored in a memory local to said processor 220.

The method then proceeds to step 410.

Step 410: Communicate Results

As an optional step, the mass of gas can be displayed in a number of ways. For example, a screen attached to the gas cylinder 100 or valve 104 could display the mass of gas contained within the gas cylinder 100. In the alternative, the mass of gas measurement could be communicated remotely to a base station or to a meter located on an adjacent fitting.

The method then proceeds to step 412.

Step 412: Power Down Sensor Assembly

It is not necessary to keep the sensor assembly 200 operational at all times. To the contrary, it is beneficial to reduce power consumption by switching the sensor assembly 200 off when not in use. This prolongs the life of the battery 206.

The configuration of the drive circuit 204 enables the quartz crystal oscillator 202 to be restarted irrespective of the gas pressure in the gas cylinder 100. Therefore, the sensor assembly 200 can be shut down as and when required in order to save battery power.

The method described above is in relation to a single measurement of the contents of the cylinder 100. Whilst the housing 250 of the present invention is arranged to shield against convective currents which affect most prominently mass flow measurements, the housing 250 will also assist in steady state contents measurement (i.e. a single measurement). This is because a user may require a steady state measurement of the true contents of a cylinder 100 after a particular flow has been drawn so that the remaining gas mass can be determined.

However, after flow has been drawn, the top of the cylinder 100 may be colder than the remainder thereof, setting up convective currents within. The housing 250 enables accurate measurement to be made of the true mass contents irrespective of the convection within the cylinder 100. This improves the accuracy and speed of steady-state measurements.

The method of operation of an embodiment of the present invention has been described above with reference to step 400 to 412 above in relation to steady state measurements. However, the following additional steps may also optionally be made in order to measure mass flow from the cylinder 100:

Steps 414-418: Make Further Determination of Mass

It may be desired to calculate the mass flow of gas to/from the gas cylinder 100. At a time $T_2$ which is later than $T_1$, steps 414, 416 and 418 are carried out. Steps 414, 416 and 418 correspond to steps 404, 406 and 408 respectively carried out at time $T_2$. The resulting values from steps 414, 416 and 418 are stored in the internal memory of the processor 220 as a mass of gas at time $T_2$.

The time interval between $T_1$ and $T_2$ may be very short, of the order of seconds as illustrated by FIG. 9. Alternatively, if the flow rate is slow, or if it is desired to measure losses within the gas cylinder 100 due to, for example, leaks, then the time interval between $T_1$ and $T_2$ may be considerably greater; for example, of the order of minutes, hours or days.

The method then proceeds to step 420.

Step 420: Apply Numerical Filtering

This step is, as described above, optional. Numerical filtering may be selected in situations where a highly accurate flow rate is required but where the response time of the measurement apparatus is less critical. Such a situation may occur when, for example, a low flow rate is being measured over a long time period.

If numerical filtering is selected, it may be carried out by dedicated computational hardware forming part of the processor 220 or alternatively may be encoded in software run on the processor 220.

As described above, the numerical filtering may comprise an exponential filter which uses the measurement made in step 406 (and stored in step 408) together with the later measurement made in step 416 (and stored in step 418).

The method then proceeds to step 422.

Step 422: Calculate Mass Flow

Knowing the time difference between times $T_1$ and $T_2$, and the mass of gas in the gas cylinder 100 at those times, the processor 220 can calculate the mass flow in the period of time between $T_1$ and $T_2$ from equation 6).

The method can then perform repeat steps 314 to 320 to calculate further mass flow if required. Alternatively, the method can move to step 312 and the sensor assembly 200 can be powered down.

Variations of the above embodiments will be apparent to the skilled person. The precise configuration of hardware and software components may differ and still fall within the scope of the present invention. The skilled person would be readily aware of alternative configurations which could be used.

Figure 17:
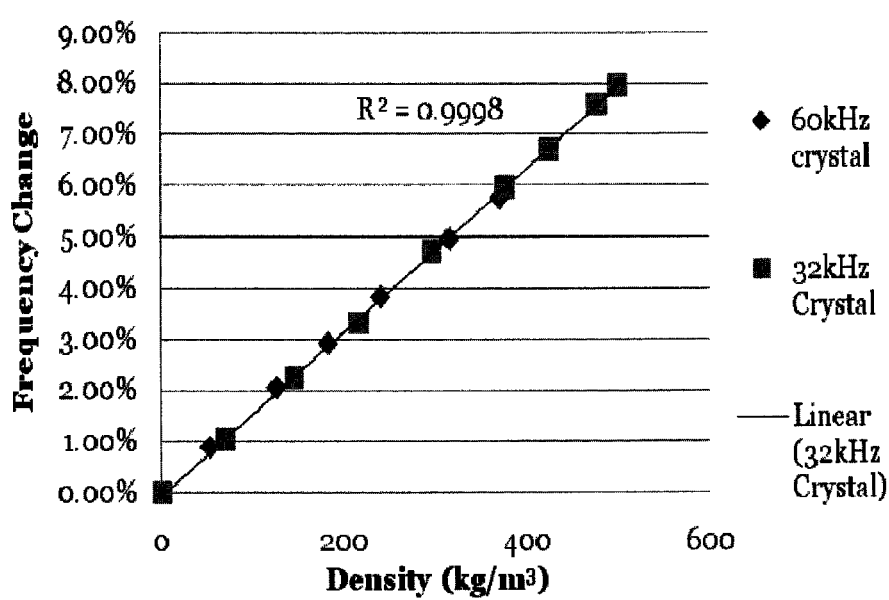
FIG. 17 shows a graph of the frequency behaviour of different crystal types.

For example, the above described embodiments have utilised a quartz crystal oscillator having a fundamental frequency of 32.768 kHz. However, crystals operating at alternative frequencies may be used. For example, quartz crystal oscillators operating at 60 kHz and 100 kHz may be used with the embodiments described above. A graph showing the frequency change with density for different crystals is shown in FIG. 17. As a further example, a crystal oscillator operating at a frequency of 1.8 MHz could be used.

Higher frequency operation enables the pressure to be monitored more frequently because a shorter time period is required to sample a given number of cycles. Additionally, higher frequency crystals enable a smaller duty cycle to be used in a "sleep" mode of a crystal. By way of explanation, in most cases, the crystal and drive circuit will spend most of the time switched off, only being switched on for a second or so when a measurement is needed. This may occur, for example, once a minute. When a higher frequency crystal is used, the pressure can be measured faster. Therefore, the time in which the crystal is operational can be reduced. This may reduce power consumption and concomitantly improve battery life.

Additionally, the above embodiments have been described by measuring the absolute frequency of a quartz crystal oscillator. However, in self-contained electronics incorporated in a gas cylinder associated regulator, it may advantageous to measure the shift in frequency of the sensor by comparing that frequency with a reference crystal of identical type but enclosed in a vacuum or pressure package. The pressure package may contain gas at a selected density, gas under atmospheric conditions or may be open to the atmosphere external of the gas cylinder 100.

Figure 18:
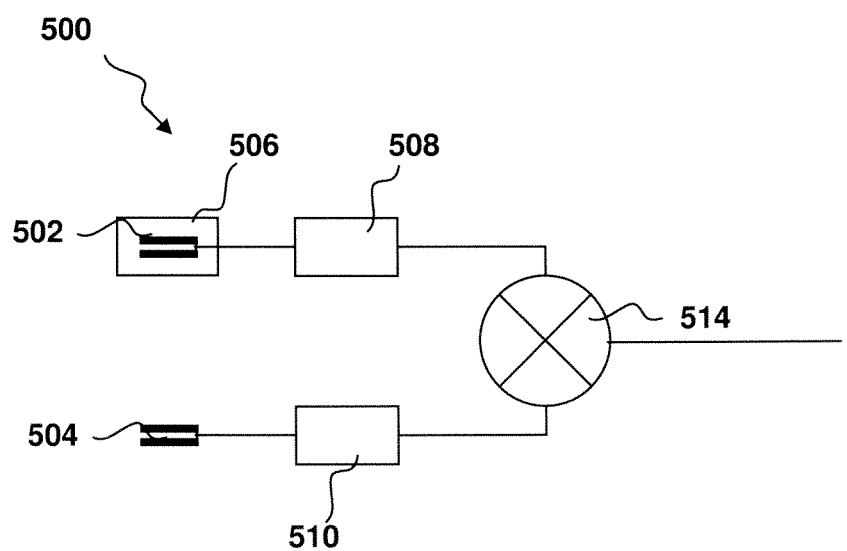
FIG. 18 is a schematic diagram showing an alternative sensor assembly comprising two quartz crystals.

A suitable sensor assembly 500 is shown in FIG. 18. The sensor assembly 500 comprises a first quartz crystal oscillator 502 and a second quartz crystal oscillator 504. The first quartz crystal oscillator 502 is a reference crystal which is located within a sealed container 506 under vacuum. The first quartz crystal oscillator 502 is driven by a drive circuit 508.

The second quartz crystal oscillator 504 is a crystal similar to the crystal 202 described in the earlier embodiments. The second quartz crystal oscillator 504 is exposed to the gas environment within the internal volume of the gas cylinder 100. The second quartz crystal oscillator 504 is driven by a drive circuit 510.

This comparison may be performed using an electronic mixer circuit 512 which combines the two frequency signal and produces an output at a frequency equal to the difference between the two crystals. This arrangement enables small changes due to, for example, temperature to be negated.

Further, the circuitry used in a gas cylinder 100 can be simplified because only the difference frequency is required to be measured. Further, this approach is particularly suitable for use with a high frequency (MHz) crystal oscillator, where it may be difficult to measure the crystal frequency directly.

Additionally, all of the electronics required to measure and display the density, mass or mass flow need not be mounted on or in the gas cylinder. For example, electronic functions could be split between units mounted on the cylinder permanently and units mounted on either a customer's usage station or temporarily mounted on the outlet of the cylinder such as the position normally used for a conventional flow meter.

Figure 19:
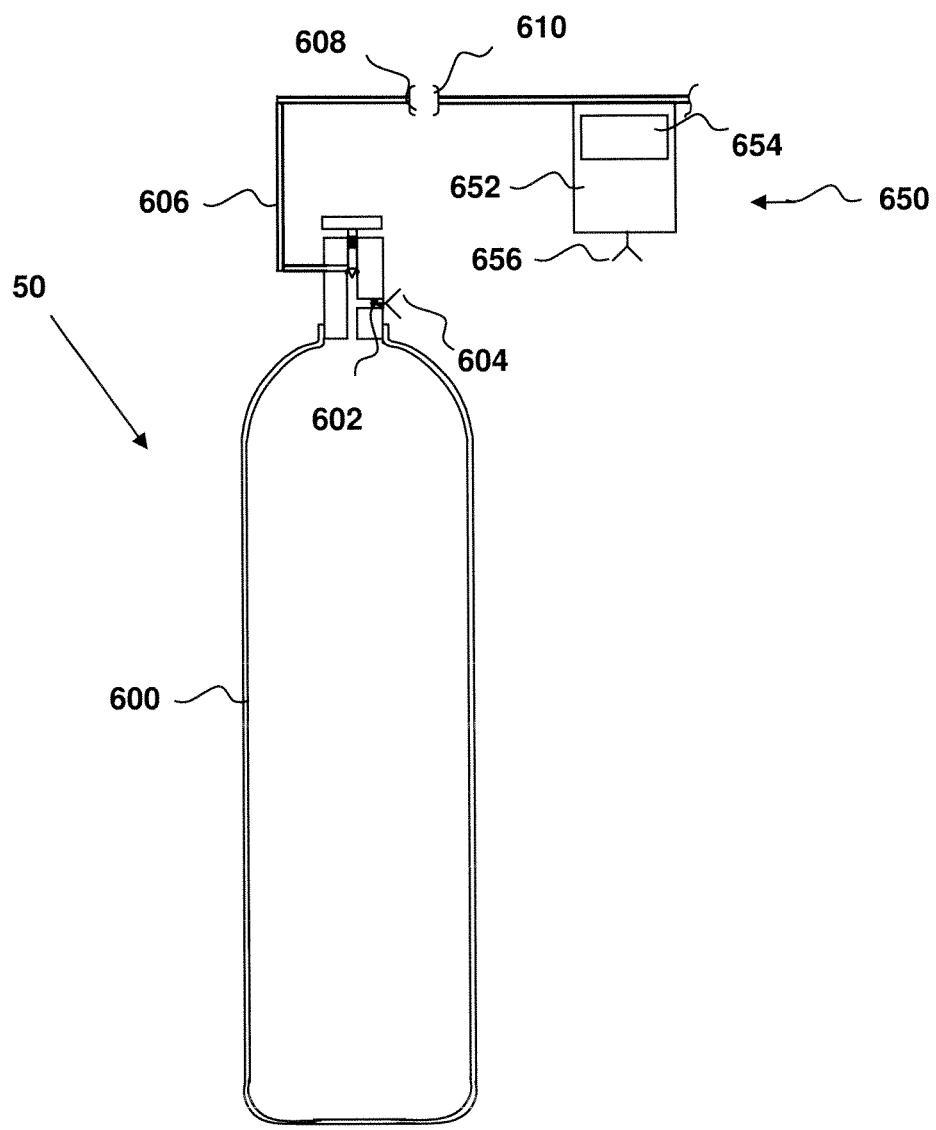
FIG. 19 shows an alternative arrangement using a remote electronic data unit.

An example of this arrangement is shown with reference to FIG. 19. The arrangement comprises a gas cylinder assembly 50 comprising a gas cylinder 600 and a sensor assembly 602. The gas cylinder assembly 50, gas cylinder 600 and sensor assembly 602 are substantially similar to the gas cylinder assembly 10, gas cylinder 100 and sensor assembly 200 substantially as previously described with reference to previous embodiments.

In this embodiment, the sensor assembly 602 comprises a quartz crystal oscillator and drive circuit (not shown) similar to the quartz crystal oscillator 202 and drive circuit 204 of earlier embodiments. An antenna 604 is provided for communication via any suitable remote communication protocol; for example, Bluetooth, Infra-red (IR) or RFID. Alternatively, one-wire communication may be utilised.

As a further alternative, acoustic communication methods may be used. The advantage of such methods is that remote communication can be effected without the requirement for an external antenna.

A connection pipe 606 is connected to the outlet of the gas cylinder 600. The connection pipe is terminated by a quick connect connection 608. The quick connect connection 508 enables connecting pipe work or components to be connected and disconnected easily and quickly from the gas cylinder 600.

A quick connect unit 650 is provided for connection to the gas cylinder 600. A complementary quick connect connector 610 is provided for connection to the connector 508. Further, the quick connect unit 650 is provided with a data unit 652. The data unit 652 comprises a display 654 and an antenna 656 for communication with the antenna 604 of the gas cylinder assembly 50. The display 654 may comprise, for example, an E-ink display to minimise power consumption and maximise visibility of the display.

The data unit 652 may log various parameters as measured by the sensor assembly 602 of the gas cylinder assembly 50. For example, the data unit 652 could log flow rate versus time. Such a log could be useful, for example, to welding contractors wishing to check that gas flow was present and correct during lengthy gas welding procedures on critical components, or to supply data on a particular customer's usage.

Additionally, the data obtained from the gas cylinder 600 may be used to present data on the run out time, i.e. the time before the gas in the cylinder 500 is used up. This is particularly critical in applications such as a hospital oxygen cylinder used in patient transit between hospitals. Such a time ($T_{ro}$) can be calculated from knowledge of the flow rate (discussed above), mass contents of the cylinder 500 and the current time ($T_c$) via the following equation 8):

$$T_{ro} = T_c + \frac{M}{\frac{\partial M}{\partial t}} \qquad 8)$$

Alternatively, data from the data unit 652 can be output to a computer-enabled welding machine (for welding applications) or other gas-using equipment, to allow the calculation of derived parameters, along with warning messages. Non-exhaustive examples of this may be: Gas used per unit arc time, gas used per kg of welding wire (eg. with warning about porosity of weld), the number of standard-size balloons (or to measure and calibrate for balloons of a non-standard size), the number of hours of welding remaining, the display of pressure (by converting the measured density value to pressure using known gas data).

Additionally, the data unit 652 may be arranged to provide the following functions: to provide an audible or visible alarm if the gas level is below a certain level or flow rate; to output the cylinder lifetime (e.g. for mixtures which change slowly) or a cylinder expiry date; to contain and display data on use of gas, i.e. which types of welding, what types of metal welded, or give links so that mobile phones or computers can pick up detailed data; to provide multimode operation, e.g. a supplier/filler mode and a customer mode; to display different quantities to the customer from that which is displayed by the gas company which refills the cylinders; to allow input of data; to provide data such as a cylinder number, the type of gas, a certificate of analysis, a customer history (who had the cylinder over what dates), safety data and operational tips can be carried in summary form on the cylinder.

As an alternative, all of the above examples may, optionally, be processed, stored or obtained from a system located entirely on (or within) the gas cylinder 600 as discussed in terms of the sensor assembly 200, 602.

Additionally, the embodiments of the present invention may also be used to perform leak detection. A quartz crystal oscillator is particularly suitable to this task due to the great sensitivity of such a sensor. Additionally, a quartz crystal oscillator will not incorrectly read pressure changes due to changes in the temperature of the cylinder, as is the case when sensing leaks using a pressure gauge. Additionally, embodiments of the invention can be used to detect failures, for example, in detection of residual pressure valve failure (e.g. in a used cylinder with pressure below 3 bar g).

Whilst the above embodiments have been described with reference to the use of a quartz crystal oscillator, the skilled person would be readily aware of alternative piezoelectric materials which could also be used. For example, a non-exhaustive list may include crystal oscillators comprising: lithium tantalate, lithium niobate, lithium borate, berlinite, gallium arsenide, lithium tetraborate, aluminium phosphate, bismuth germanium oxide, polycrystalline zirconium titanate ceramics, high-alumina ceramics, silicon-zinc oxide composite, or dipotassium tartrate.

Additionally, whilst the above embodiments have been illustrated with reference to gas cylinders, other applications of the present invention may be utilised. For example, the quartz crystal oscillator may be located within the tyre of a vehicle such as a car, a motorbike or a truck. Whilst the shape of the tyre of a vehicle may change under load or at speed, the inventors of the present application have shown that the internal volume of the tyre does not change significantly in use. For example, provided that the change in internal volume is, in this context, less than 2-3% of the total internal volume, the present invention is reliably operable to calculate the mass of gas within a tyre of the vehicle.

Further, whilst many applications use air as the gas within a vehicle tyre, increasingly, gases such as Nitrogen are used. The arrangements of the present invention are particularly suitable to such applications. Further, because the measurement of mass is essentially independent of temperature, the arrangement of the present invention is particularly useful in situations where environmental conditions may affect measurements.

As a further example, the present invention may also be applicable to air suspension systems for vehicles.

Embodiments of the present invention have been described with particular reference to the examples illustrated. While specific examples are shown in the drawings and are herein described in detail, it should be understood, however, that the drawings and detailed description are not intended to limit the invention to the particular form disclosed. It will be appreciated that variations and modifications may be made to the examples described within the scope of the present invention.

The invention claimed is:

1. A sensor assembly for measuring physical properties of a gas under pressure within a gas cylinder comprising: a gas cylinder body and a valve arrangement defining a fixed internal volume of the gas cylinder, the sensor assembly comprising a housing, a piezoelectric oscillator for immersion in the gas within the gas cylinder and a drive circuit operable to drive the piezoelectric oscillator such that the piezoelectric oscillator resonates at a resonant frequency, the sensor assembly being arranged to determine the density of the gas within the gas cylinder from the resonant frequency of the piezoelectric oscillator when immersed in said gas, wherein, in use, the housing is located within the fixed internal volume of the gas cylinder and comprises a first chamber and a second chamber, the first chamber being in fluid communication with the second chamber and substantially enclosing said piezoelectric oscillator, and the second chamber being in fluid communication with the interior of the gas cylinder;

wherein the sensor assembly further comprises a processor arranged to determine, from the density measurement and from the internal volume of said gas cylinder, the mass of the gas within the gas cylinder.

2. A sensor assembly according to claim 1, wherein the processor is further arranged to perform repeat measurements of the mass of the gas within the gas cylinder at discrete time intervals to obtain a plurality of measurements, and to determine, from said plurality of measurements, the mass flow of gas to/from the gas cylinder during the discrete time intervals.

3. A sensor assembly according to claim 2, wherein the processor is arranged to define said discrete time intervals as of the order of seconds.

4. A sensor assembly according to claim 2, wherein the processor is arranged to apply numerical filtering to said measurements.

5. A sensor assembly according to claim 1, wherein the first chamber has a wall comprising a first aperture enabling fluid communication between the first and second chambers, and the second chamber has a wall comprising a second aperture to enable fluid communication between the second chamber and the interior volume of the gas cylinder.

6. A sensor assembly according to claim 5, wherein the first and/or second aperture has dimensions of 0.35 mm or less.

7. A sensor assembly according to claim 6, wherein the first and/or second aperture has dimensions of 0.22 mm or less.

8. A sensor assembly according to claim 1, wherein the housing is substantially cylindrical.

9. A sensor assembly according to claim 1, wherein the housing has a length of 230 mm or less.

10. A sensor assembly according to claim 9, wherein the housing has a length of 80 mm or less.

11. A sensor assembly according to claim 1, wherein said piezoelectric oscillator comprises a quartz crystal oscillator.

12. A gas cylinder for containing a gas under pressure, the gas cylinder comprising:
a gas cylinder body defining a fixed internal volume;
a valve arrangement connected to said gas cylinder body and arranged to enable one or both of selective filling of the gas cylinder with gas and dispensation of gas from said gas cylinder; and
the sensor assembly of claim 1.

13. A gas cylinder according to claim 12, wherein the sensor assembly is located entirely within the fixed internal volume of the gas cylinder.

* * * * *